United States Patent [19]
Katz

[11] Patent Number: 6,059,788
[45] Date of Patent: May 9, 2000

[54] METHOD AND APPARATUS FOR LOCATING BONE CUTS AT THE DISTAL CONDYLAR FEMUR REGION TO RECEIVE A FEMORAL PROSTHESIS AND PROPERLY ARTICULATED WITH PATELLAR AND TIBIAL PROSTHESIS

[76] Inventor: Lawrence Katz, 10 Iron Latch West, Upper Saddle River, N.J. 07458

[21] Appl. No.: 08/956,015

[22] Filed: Oct. 22, 1997

Related U.S. Application Data

[63] Continuation of application No. 08/455,985, May 31, 1995, Pat. No. 5,776,137.

[51] Int. Cl.$^7$ ..................................................... A61B 17/58
[52] U.S. Cl. .............................. 606/88; 606/87; 606/102
[58] Field of Search ................................ 606/87, 88, 102, 606/89

[56] References Cited

U.S. PATENT DOCUMENTS

| | | |
|---|---|---|
| 4,950,298 | 8/1990 | Gustilo et al. . |
| 5,047,058 | 9/1991 | Roberts et al. . |
| 5,053,037 | 10/1991 | Lackey . |
| 5,100,408 | 3/1992 | Lackey . |
| 5,234,433 | 8/1993 | Bert et al. . |
| 5,282,803 | 2/1994 | Lackey . |
| 5,354,075 | 10/1994 | Marik et al. . |
| 5,364,401 | 11/1994 | Ferrante et al. . |
| 5,417,694 | 5/1995 | Marik et al. . |
| 5,454,816 | 10/1995 | Ashby . |
| 5,484,446 | 1/1996 | Burke et al. . |
| 5,486,178 | 1/1996 | Hodge . |
| 5,514,140 | 5/1996 | Lackey . |
| 5,549,688 | 8/1996 | Ries et al. . |
| 5,776,137 | 7/1998 | Katz ........................................... 606/88 |

*Primary Examiner*—Michael Buiz
*Assistant Examiner*—Julian W. Woo
*Attorney, Agent, or Firm*—Ostrolenk, Faber, Gerb & Soffen, LLP

[57] ABSTRACT

An apparatus for forming planar resections on the medial and lateral condyles of a femur includes a caliper feeler and measurement plate to measure for the size of the femoral prosthesis to be received, said caliper feeler and measurement plate adapted to determine a first distance between an anterior surface of the femoral cortex and a plane tangent to a posterior surface of the medial and lateral condyles of a femur. A graduated scale compares the first distance to at least two standard femoral prosthesis sizes and determines the smaller of the at least two standard femoral prosthesis sizes. A graduated scale measures a second distance between the first distance and the size of the smaller standard femoral prosthesis size, so that a thickness or thicknesses can be measured to be resected at the posterior surface of the medial and lateral condyles of the femur by adding the average thickness of the posterior condyles of the smaller standard femoral prosthesis and the second distance.

29 Claims, 26 Drawing Sheets

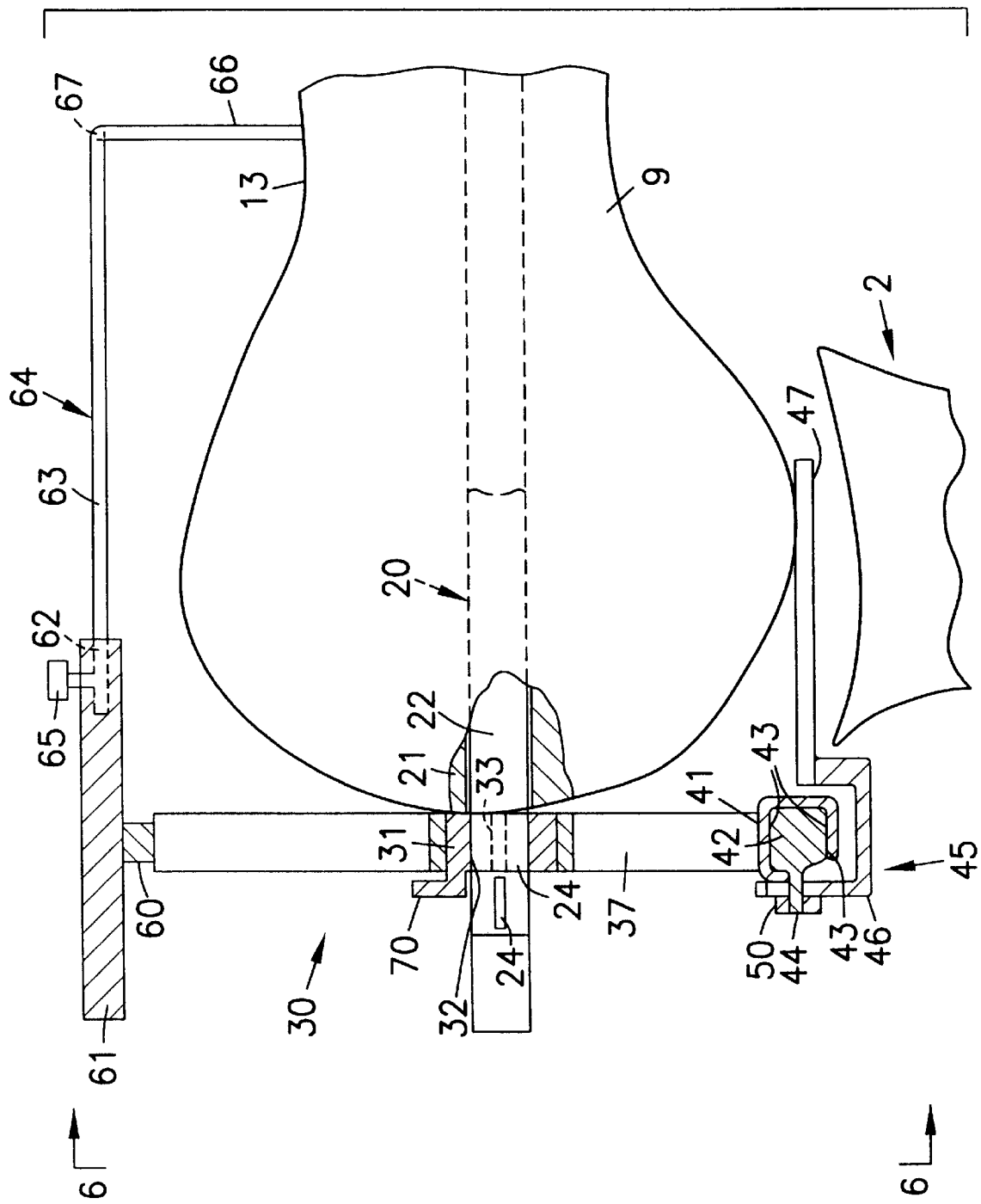

METHOD AND APPARATUS FOR LOCATING BONE CUTS AT THE DISTAL CONDYLAR FEMUR REGION TO RECEIVE A FEMORAL PROSTHESIS AND PROPERLY ARTICULATED WITH PATELLAR AND TIBIAL PROSTHESIS

CROSS REFERENCE TO RELATED APPLICATIONS

This application is a continuing application to U.S. Pat. application Ser. No. 08/455,985, filed May 31, 1995, now U.S. Pat. No. 5,776,137 entitled METHOD AND APPARATUS FOR LOCATING BONE CUTS AT THE DISTAL CONDYLAR FEMUR REGION TO RECEIVE A FEMORAL PROSTHESIS, now pending.

FIELD OF THE INVENTION

The invention relates to methods and apparatus for locating bone cuts on the medial and lateral femoral condyles to form seating surfaces for a femoral knee prosthesis.

The invention further relates to a tool for locating said cuts.

In particular, the invention relates to such method, apparatus and tool which enable planar cuts to be made at the anterior surfaces, the posterior surfaces and the distal ends of the medial and lateral condyles of the femur to form seating surfaces to receive the femoral knee prosthesis.

BACKGROUND OF THE INVENTION

Over the years, the concepts of designs for the total knee arthroplasty have evolved to the point where with few exceptions, most are quite comparable in the design of femoral, tibial and patellar prostheses.

Major discrepancies and problems encountered are caused by physician error and failure to understand the principles of more complex alignment or ligament problems to be corrected at surgery. With the more complex alignment or "routine" degenerative knee, the major differences are the ease and consistency of instrumentation for alignment and proper bone cuts allowing proper ligament balance. This allows satisfactory motion and stability post operatively.

The distal femoral cuts must be placed to provide the knee prosthesis with a proper flexion and extension gap, proper varus-valgus alignment, proper patellofemoral relationship and proper rotation. It is customary to use an intramedullary rod placed in a retrograde fashion between the medial and lateral femoral condyles just anterior to the intercondylar notch to establish a single point of reference for subsequent bone cuts. A major problem is in the instrumentation to indicate the location of the femoral cuts which relies upon the "experience" or "eyeballing" of the surgeon. Over the years, two basic instrument system designs have become popular.

In one design (anterior referencing), the total knee alignment system takes its point of reference from a centrally placed rod and careful attention is given to the patellofemoral joint by using an anteriorly placed feeler gage. The distal femoral cut is consistent with the thickness of the prosthesis.

This instrument system operates on the principle of anatomic anterior and distal femoral cuts to allow proper ligament balancing and stability in extension as well as consistent patellofemoral placement on the anterior surface. The femur is not notched, and the anterior surface of the femoral prosthesis not elevated above the anterior surface of the femur. Notching the femur may cause a decrease in strength of the distal femur. Elevation of the anterior surface of the prosthesis will cause extremely high patellofemoral pressures in a joint that seems to be prone to a high rate of post-operative failure.

By establishing the anterior femoral cut as the benchmark or datum starting point, however, the anterior referencing instruments result in the installation of a knee prosthesis which sacrifices consistent stability in flexion due to the formation of a posterior femoral condylar cut that may leave the posterior space either too wide or too narrow. This can cause instability in flexion, or restrict flexion and cause increased wear.

The second type of instrument design (posterior referencing) is based on the concept that the flexion and extension stability are more important and the patellofemoral joint is of secondary importance. This system also uses an intramedullary rod for referencing. Although I consider all three joints as "important", when a compromise must be made, the posterior referencing systems compromise the patellofemoral joint while the anterior reference systems sacrifice stability in flexion (the posterior tibial femoral joint). Both systems allegedly equally address the distal tibial-femoral space. Neither consistently addresses the distal rotation of the femoral component.

SUMMARY OF THE INVENTION

An object of the invention is to provide methods and apparatus enabling the formation of planar cuts on the medial and lateral femoral condyles for the femur to provide seating surfaces for a femoral knee prosthesis which reliably and anatomically provide:

1. Consistent distal tibio-femoral stability.
2. Consistent distal femoral rotation.
3. Consistent placement of the anterior cut flush with the anterior surface of the femoral cortex, i.e., without notching or elevation.
4. Consistent placement of the posterior femoral cut such that the distal and posterior cuts are equal (when indicated) allowing for satisfactory extension and flexion stability and motion.

The method and apparatus of the invention contemplate placement of the anatomic joint line which, in extreme cases, vary up to the difference between the anterior-posterior A-P internal measurements of the size prostheses. Based on my knowledge of total knee replacement, personal experience with numerous routine total knee replacements, numerous more complicated cases consisting of knees with flexion deformities and revision surgery, a maximum of a few mm proximal displacement of the joint line is considerably less harmful than:

1. A lax flexion gap;
2. Sloping the proximal tibial cut to accommodate for an inconsistent posterior femoral condylar cut;
3. Significantly notching the femur anteriorly;
4. Raising the anterior flanges of the prosthesis and thus the patellofemoral joint;
5. Not allowing full extension;
6. Raising the joint line;
7. Tightness in flexion;
8. Malrotation; and
9. Patient pain.

In accordance with the invention, a method is provided for forming planar cuts on the medial and lateral condyles of the femur to form seating surfaces to receive a femoral knee prosthesis, comprising:

determining a prospective planar cut at the posterior of the condyles of the femur at which the distance between the anterior surface of the femoral cortex and the prospective planar cuts is substantially equal to the interior dimension of a knee prosthesis to be fitted on said femur at the anterior surface and the cut planar surface, determining the thickness of the posterior lateral or medial condyle which will be resected by said prospective planar cut, cutting the distal ends of the condyles along a plane at which the maximum thickness of resection of the more prominent condyle at said distal end is substantially equal to the thickness determined to be resected at the posterior medial or lateral condyle by said prospective planar cut, and cutting the condyles along a plane substantially flush with the anterior surface of the femoral cortex, and along said prospective planar cut.

The method further contemplates loosely placing a longitudinal intramedullary rod in the femur such that an end of the rod projects from the femur, mounting a tool on the projecting end of the rod, establishing, by said tool, an angular position of said prospective planar cut along a plane rotated at an angle of between 0 and 15" with respect to a tangential plane at the posterior of the lateral and medial condyles about an axis located in said tangential plane.

In further accordance with the method, the tool is rotated with said rod through said angle and a datum or benchmark is established by the rotated rod or by pins installed in the condyles on the basis of the rotated position of the tool. A cutting guide can be mounted on said tool, to enable the distal end of the condyles to be cut along said plane. Thereafter, the tool is removed and a second A-P cutting guide is mounted on the selected benchmark, i.e., the rod or the pins and the posterior and anterior cuts are made. The axis about which the plane of the prospective cut is rotated is located in said tangential plane at the posterior surfaces of the medial and lateral condyles and can be located at either of the condyles or at any location therebetween. It is a feature of the invention that the tool remains on the rod both for the measurements and for the cutting of the distal end of the femur.

The invention also contemplates that the cutting guide supports a means which enables the cutting guide to be secured to the condyles during the cutting of the distal ends of the condyles.

The invention further contemplates an apparatus for forming planar resections on the medial and lateral condyles of a femur to form seating surfaces to receive a femoral prosthesis and to properly articulate with a tibial and patellar prosthesis comprises:

a caliper feeler and measurement plate to measure for the size of the femoral prosthesis to be received, said caliper feeler and measurement plate adapted to determine a first distance between an anterior surface of the femoral cortex and a plane tangent to a posterior surface of the medial and lateral condyles of a femur, the caliper feeler referencing the anterior surface of the femoral cortex and the measurement plate referencing the plane tangent to the posterior surface of the medial and lateral condyles;

a graduated scale to compare the first distance to at least two standard femoral prosthesis sizes and to determine the smaller of the at least two standard femoral prosthesis sizes;

a graduated scale to measure a second distance between the first distance and the size of the smaller standard femoral prosthesis size, so that a thickness or thicknesses can be measured to be resected at the posterior surface of the medial and lateral condyles of the femur by adding the average thickness of the posterior condyles of the smaller standard femoral prosthesis and the second distance;

a tool to resect the medial and lateral condyles along a plane at the anterior surfaces thereof flush with the anterior surface of the femoral cortex; and a tool to resect distal ends of the medial and lateral condyles at a resected thickness equal to the average thickness of the distal condyles of the smaller standard femoral prosthesis plus the second distance.

The apparatus further contemplates a tool to resect the measured thickness at the posterior surface of the medial and lateral condyles of the femur.

The invention also contemplates a method for forming planar resections on the medial and lateral condyles of a femur to form seating surfaces to receive a femoral prosthesis and to properly articulate with a tibial and patellar prosthesis comprises:

measuring for the size of the femoral prosthesis to be received by determining a first distance between an anterior surface of the femoral cortex and a plane tangent to a posterior surface of the medial and lateral condyles of a femur;

using a graduated scale to compare the first distance to at least two standard femoral prosthesis sizes;

measuring a second distance between the first distance and the size of the smaller standard femoral prosthesis size; and measuring a thickness or thicknesses to be resected at the posterior surface of the medial and lateral condyles of the femur, the thickness being equal to the average thickness of the posterior condyles of the smaller standard femoral prosthesis plus the second distance.

The method further contemplates the steps of resecting the medial and lateral condyles along a plane at the anterior surfaces thereof substantially flush with the anterior surface of the femoral cortex; and measuring a thickness or thicknesses to be resected at the distal ends of the medial and lateral condyles, the thickness being equal to the average thickness of the distal surface of the smaller standard femoral prosthesis plus the second distance, and resecting the distal ends of the medial and lateral condyles at the measured thickness.

Other features and advantages of the present invention will become apparent from the following description of the invention which refers to the accompanying drawings.

BRIEF DESCRIPTION OF THE DRAWINGS

FIG. 5 is a side view similar to FIG. 1 in which the tibia has been turned 90° to expose the distal end of the femur, an intramedullary rod has been inserted into the femur and a tool placed on the rod, the tool being partly broken away and shown in section.

DETAILED DESCRIPTION OF THE INVENTION

Figure 1:
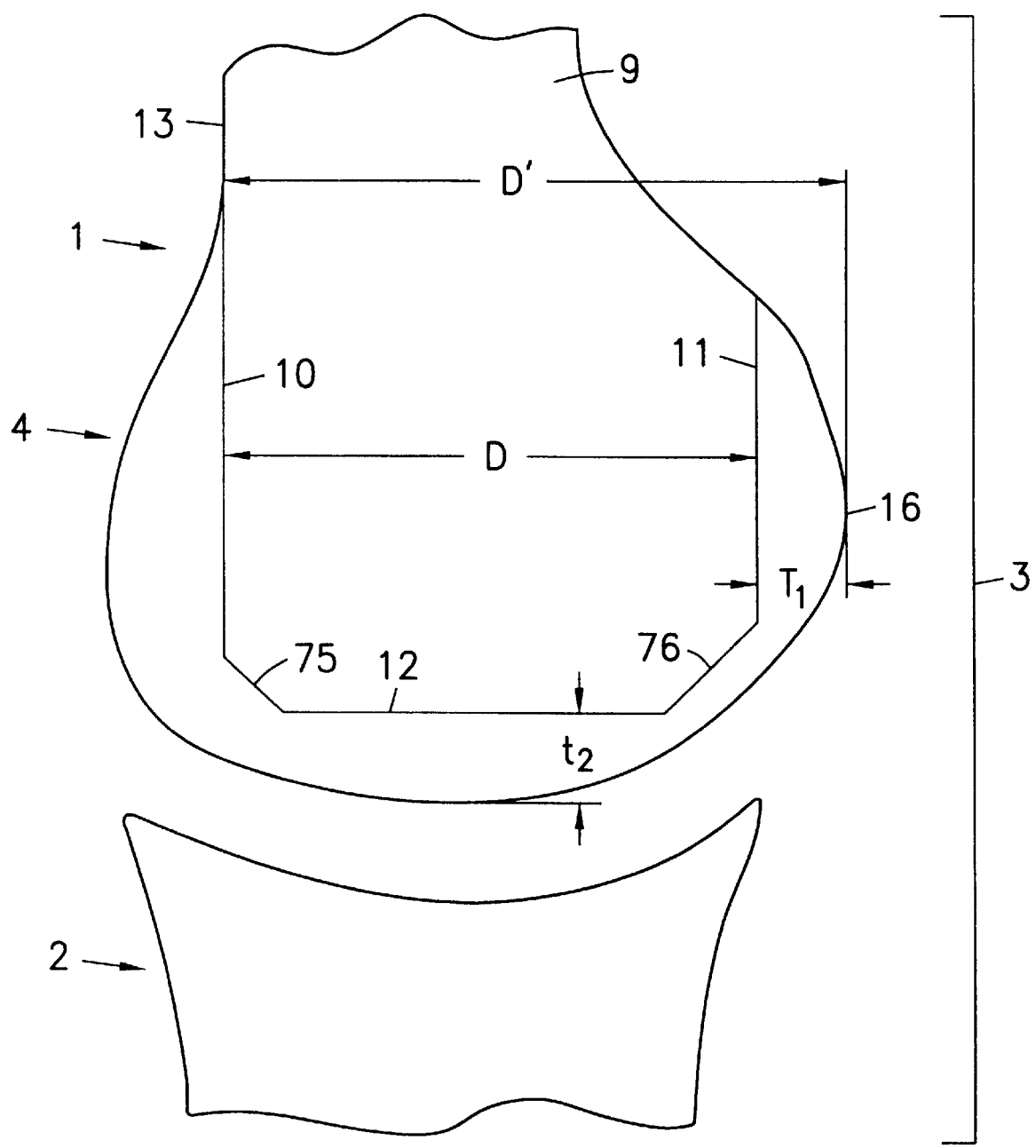
FIG. 1 is a diagrammatic, lateral view of the femur and tibia at a knee joint showing prospective cuts to be made on the femur for installation of a femoral prosthesis.
Figure 4:
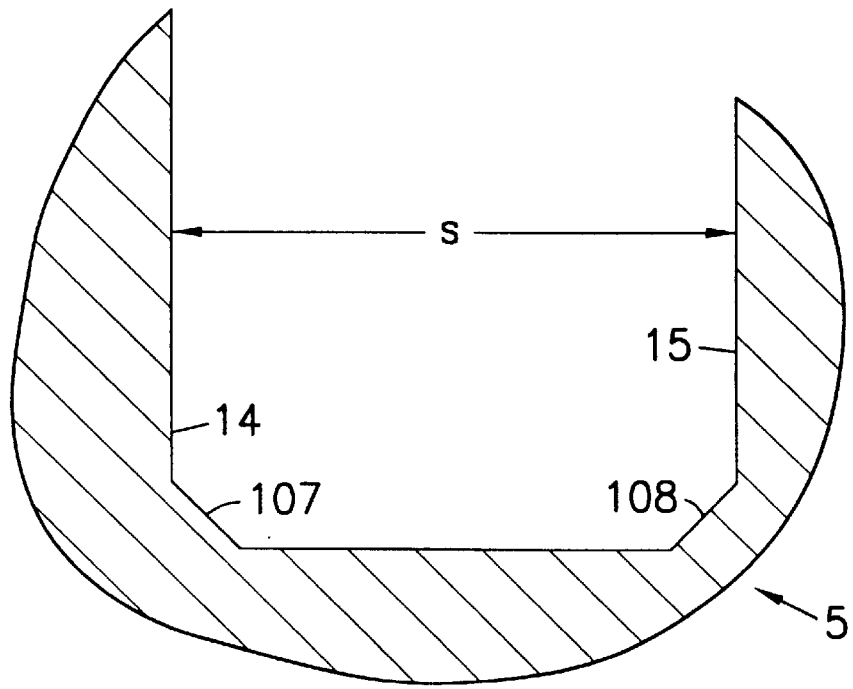
FIG. 4 is a sectional view of a femoral knee prosthesis adapted for placement on the femur after the planar cuts have been made on the femur.

Referring now to FIG. 1, the drawing diagrammatically illustrates the femur 1 and tibia 2 of a knee joint 3. The invention is concerned with the placement of planar resections or cuts at the distal condylar region 4 of the femur 1 to receive a femoral knee prosthesis 5 (FIG. 4). Typically, a total knee replacement also requires placing a planar cut at the proximal tibia of the tibia 2 to receive a tibial prosthesis, not shown. The tibial prosthesis typically consists of a tibial baseplate, not shown, that is fitted on the proximal tibia after the tibial cut is made, and an articular insert, not shown, secured to the baseplate to articulate with the femoral prosthesis 5.

The cut made on the tibia 2 and installation of the tibial knee prosthesis should be as close to the anatomic level as possible and should be substantially parallel to the floor in the mediolateral plane. This maintains the joint line at or close to anatomic level. Moreover, the angle of the proximal tibial resection should correspond to the angle of the distal femoral resections 12. For example, the proximal tibial is in mild varus and is resected such that the resection in the mediolateral plane is parallel to the floor and oriented posteriorly about 3°. Accordingly, the cuts made on the femoral prosthesis, discussed below, must also take into account this 3° mediolateral orientation in order to align the femoral prosthesis with the tibial prosthesis as will be explained later.

It is also important that the resected space medially in extension between the tibia 2 and the femur 1 of the knee equals the combined thickness of the medial tibial prosthesis and the distal medial femoral prosthesis; that the resected space laterally in extension between the tibia 2 and the femur 1 of the knee equals the combined thickness of the lateral tibial prosthesis and the distal lateral femoral prosthesis; that the resected space medially in flexion between the tibia 2 and the femur 1 of the knee equals the combined thickness of the medial tibial prosthesis and the posterior medial femoral prosthesis; that the resected space laterally in flexion between the tibia 2 and the femur 1 of the knee equals the combined thickness of the lateral tibial prosthesis and the posterior lateral femoral prosthesis; and that the resected space between the tibia 2 and the femur 1 of the knee in flexion must be equal to or greater than the resected space between the tibia 2 and the femur 1 of the knee laterally in extension, assuming normal ligament balance.

The condylar region 4 of the femur 1 is formed with a medial condyle 6 and a lateral condyle 7 separated by an intercondylar notch 8. The femur 1 includes a shaft 9 forming the femoral cortex, the condylar region 4 being at the distal end of the shaft 9.

In order to install the femoral knee prosthesis 5 on the distal condylar region 4 of the femur 1, three planar cuts are made in the condylar region 4 to form seating surfaces for the prosthesis 5. These cuts consist of an anterior cut 10, a posterior cut 11 and a distal end cut 12. The placement of these cuts 10, 11, 12 is crucial to the installation of the prosthesis 5 and its effect on the overall function of the prosthetic knee joint.

The invention is based on complying with the following conditions.

1. Forming the planar cut 10 at the anterior surface of the femoral condylar region flush with the anterior surface 13 of the femoral cortex so as to form a continuous surface therewith free of formation of either a notch or elevation at the juncture of cut 10 and surface 13.

2. Forming the planar cut 11 at the posterior surface of the femoral condylar region at a distance D from planar cut 10 equal to the interior dimension S between the anterior and posterior mounting surfaces 14, 15 of the prosthesis 5. The dimension S is the so-called A-P distance of the prosthesis and this distance varies for different size prosthesis. For example, prosthesis are categorized as small, small(+), medium, large, large(+) and extra large and the A-P distance increases in proportion to the size increase.

Figure 3:
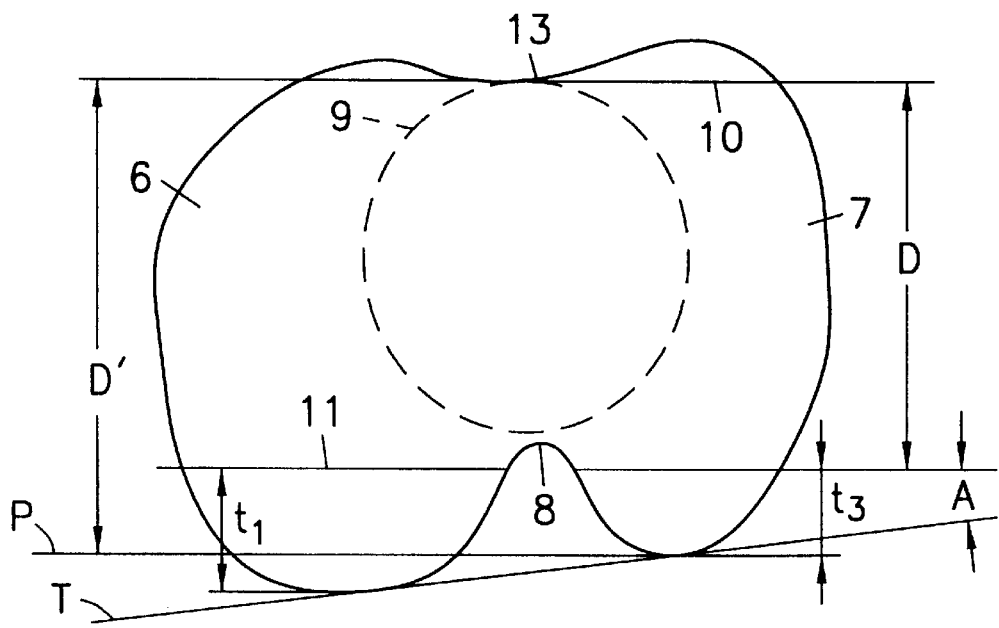
FIG. 3 is an end view from the distal end of the femur of the knee joint.

With reference to FIG. 3, therein is seen a plane T tangential to the medial and lateral condyles at the posterior surface 16 of the condylar region. The planar cut 11 is made at an angle A, with respect to plane T to angularly align the femoral prosthesis with the tibial prosthesis. Normally, the angle would be 3° to match the angle of the tibial prosthesis, however, due to anatomical conditions of the patient such as wear of the medial or lateral condyles posteriorly the angle A can vary substantially, generally between 0 and 15°. The planar cut 11 will result in resection of bone of a thickness $t_1$ at the medial condyle 6 and a thickness $t_3$ at the lateral condyle. The thickness $t_3$ is usually less than $t_1$ and controls the location of planar cut 11 so that a minimum thickness of bone is resected at the posterior surfaces of the condyles. In this regard, the thickness $t_3$ is established as the difference between distance D' between the anterior surface 13 of the femoral cortex and a plane P tangent to the posterior surface of the lateral condyle 7 and parallel to planar cut 11 and distance D between the anterior surface of the femoral cortex 13 and planar cut 11.

The thickness $t_3$ and the location of the prospective planar cut 11 therefore can be established based on measurement of the distance D and the A/P dimension of the selected size of the prosthesis. The size of the prosthesis is determined on the basis of the measurement of the distance D' and in general, the prosthesis size will be selected so that the thickness $t_3$ falls within a relatively narrow range, generally at least 6 mm and between 6 and 11 mm. The resected thickness of bone $t_1$ and $t_3$ at the medial and lateral condyles are generally unequal.

The distal end cut 12 is made so that the maximum thickness $t_2$ of bone resected at the distal end is substantially equal to $t_3$, i.e., the maximum thickness $t_2$ of bone resected at the more prominent condyle at the distal end (the medial condyle 6 in FIG. 2) is equal to the minimum thickness $t_3$ of bone resected at the posterior surface.

Referring now to FIG. 5, in order to establish the precise positions of the three planar cuts 10, 11, 12 to be made on the femur 1, a referencing or datum system is utilized which in the description herein is in the form of an intramedullary rod 20 installed in a bore 21 formed in the femur 1. The use of the intramedullary rod 20 as a benchmark or datum is known in the art and is illustrated herein by way of example. Other referencing or datum systems can be employed as well, for example, utilizing two pins placed in the condyles as set distance below the anterior femoral cut to position an AP cutting guide thereon. This will be described later.

Figure 7:
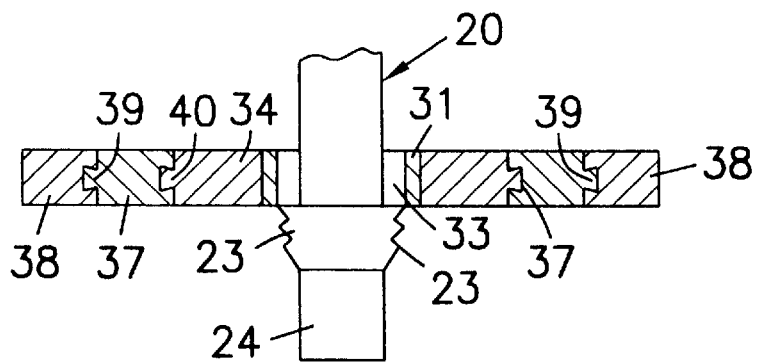
FIG. 7 is a sectional view taken on line 7—7 in FIG. 6.

The bore 21 is formed longitudinally in the shaft 9 and in the condylar region 4 of the femur 1 at a location which is slightly anterior of the intercondylar notch 8. The rod 20 has a cylindrical portion 22 which snugly fits in the bore 21 but is able to be rotated in the bore 21. The rod 20 may include radial flutes 23 extending outwardly a distance slightly greater than the diameter of the bore 21. The flutes 23 are initially outside the bore 21 and are intended to be driven into the bore 21 to fixedly secure the rod 20 in the bore 21. For this purpose, the flutes 23 are tapered to facilitate driving them into the bore 21 and grip the bore tightly in the distal femur 1 when driven therein. The outer ends of the flutes 23 can be saw-tooth or jagged as shown in FIG. 7 to provide a resilient gripping action.

The rod 20 includes an adjunct end or stub 24 which is non-circular in cross-section. The stub 24 may extend at an angle with respect to the longitudinal axis of the rest of the shaft so as to be substantially perpendicular to the joint and the prospective distal end cut 12 and parallel to the weight bearing axis of the leg. Shafts having stubs with different angles varying about 5–7° may be provided and selection is made on the sex, anatomical condition, and other conditions of the patient. This is conventional in prior usage.

The angular position of the non-circular stub 24 in bore 21 when the flutes 23 are driven into the bore 21 is a measure of the angle A at which the posterior and anterior cuts 11, 10 are made and, consequently, of the angular position of the knee prosthesis 5 on the femur 1 relative to the weight bearing axis of the leg.

The anatomical conditions governing the angular position of the rod 20 in the bore 21 is based on anatomy to maintain a straight line between the hip joint or the center of the femoral head in neutral rotation, the center of the knee joint and the midmedial third of the tibial plafond.

If the rod 20 initially assumes an angular position parallel to plane T, the rod is rotated by angle A to reach its datum position from which the cuts 10, 11, 12 will eventually be made. Nominally, the rotation is at an angle 3° to match the angle of the tibia prosthesis. However, due to wear of the condyles, and anatomical conditions of the patient the rotation of the rod must be varied from 3° to match the tibia prosthesis. The surgeon is readily able to estimate this angle based on the anatomy and on X-rays of the patient. Heretofore, however, the surgeon had to estimate the angle at which to set the rod 20 when the rod is driven into the bore 21. An imprecise estimate of the rotational orientation of the stub 24 can lead to angulation and placement errors of the prosthesis. Stated succinctly, the estimate of the surgeon of the angulation of cut 11 based on patient anatomy is accurate, but the "eyeballing" of the rotational position of the stub is often inaccurate.

The invention provides a tool or instrument 30 which is fitted on the stub 24 of rod 20 and accurately establishes rotation of the rod 20 when it is driven into the bore 21 and which measures the distance D' which in turn will determine the location of the planar cuts 10, 11, 12.

The tool 30 includes a sleeve 31 having a circular-like bore 32 of the same shape as the stub 24 in order to be fitted on the stub 24 for common rotation therewith. The bore 32 should include longitudinal slots or striations, e.g., star-shaped. The sleeve 31 has grooves 33 aligned with flutes 23 to permit passage of the flutes 23 through the sleeve 31 when the rod 20 is driven into the bore 21 in the shaft 9 of the femur 1. The sleeve 31 is rotatably supported in a slider 34 which is slidably supported by a lower half 35 of a caliper means whose upper half 36 is slidably engaged with lower half 35. The upper and lower halves 36, 35 are formed as open U-shaped members forming adjacent legs 37, 38 which are slidably engaged by tongue and groove engagement means 39. The slider 34 is slidably engaged in the legs 37 of the lower half 35 of the caliper means by a tongue and groove engagement means 40.

A cross leg 41 at the closed end of the lower half 35 of the caliper means engages a bar 42 for slidable movement in a direction substantially perpendicular to the direction of slidable movement of slider 34. The bar 42 is formed with opposed flats 43 on which the cross leg 41 can slide without undergoing rotation. The bar 42 is provided with forwardly facing pins 44 at end regions thereof.

Figure 8:
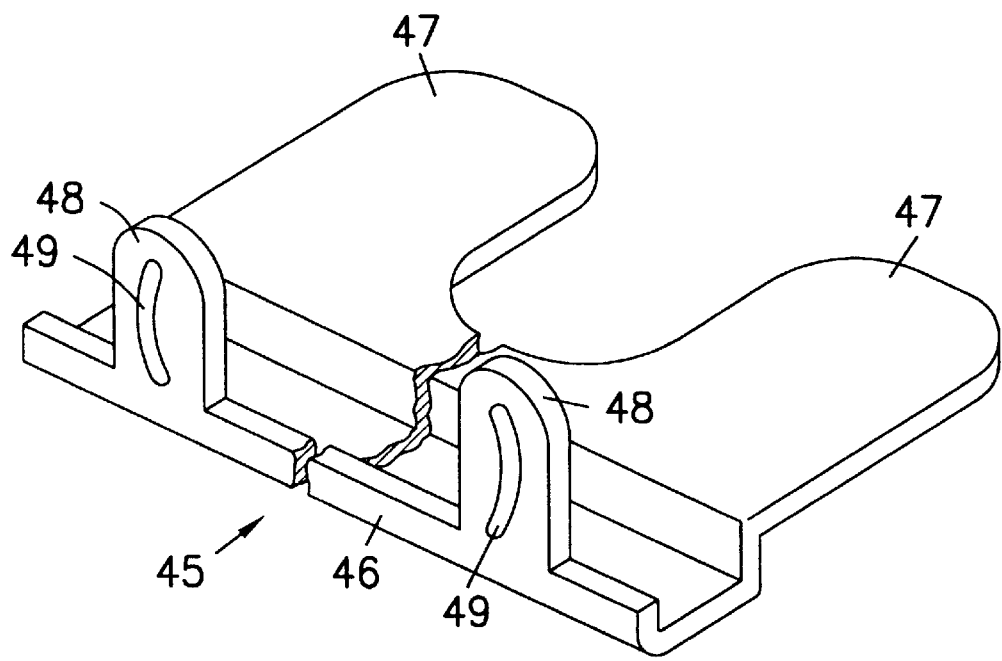
FIG. 8 is a broken, perspective view of a lower caliper feeler of the tool.
Figure 6:
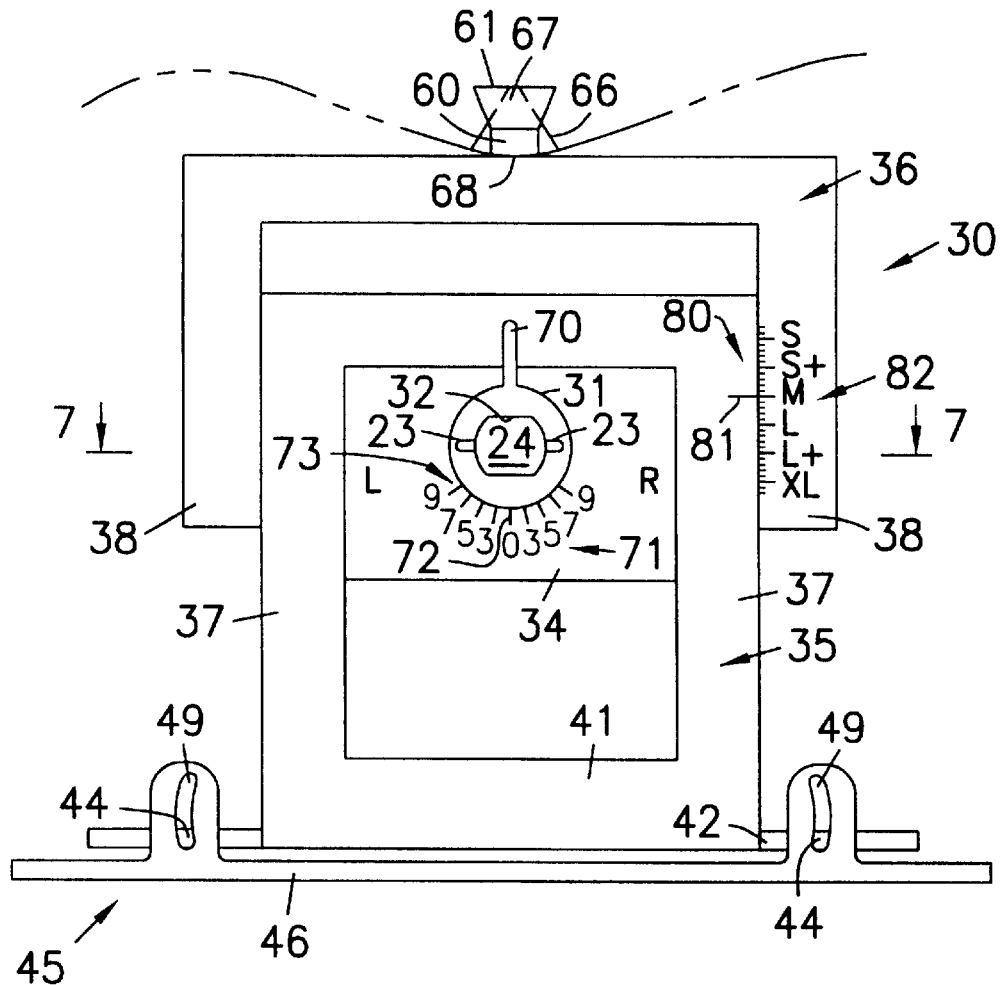
FIG. 6 is an end view of the tool taken in the direction of arrow 6—6 in FIG. 5.

A posterior caliper 45 is mounted on the pins 44. The posterior caliper 45 includes a caliper plate 46 with spaced caliper feelers 47 (FIG. 8) for respectively contacting the posterior surfaces of the medial and lateral condyles. A pair of upright legs 48 are provided on plate 46 and the legs 48 are provided with respective slots 49 to receive respective pins 44 of bar 42. The slots 49 are part-circular in extent and have a common center such that either pin 44 can ride its respective slot 49 and change the angle of bar 42 relative to the caliper plate 46. The ends of the pins 44 are threaded and nuts 50 are engaged on the threaded ends to lock the position of the pins 44 in the slots 49.

At the top of upper half 36 of the caliper means is an integral upstanding projection 60 which is integral with a guide bar 61. The guide bar 61 extends substantially perpendicular to the plane of the caliper halves 36, 37. The guide bar 61 has a bore 62 at one end thereof in which is slidably fitted an end of a rod 63 of an anterior caliper feeler 64 for extension and retraction adjustment movement of the anterior caliper feeler 64. A nut 65 secures the position of the rod 63. At the end of the rod 63 of the anterior caliper feeler 64 is a sector plate 66 which is pivotally supported at 67 by the rod 63. The sector plate 66 has a part-circular surface 68 adapted to contact the anterior surface 13 of the femoral cortex. The surface 68 has its center at the pivotable support point 67.

Figure 2:
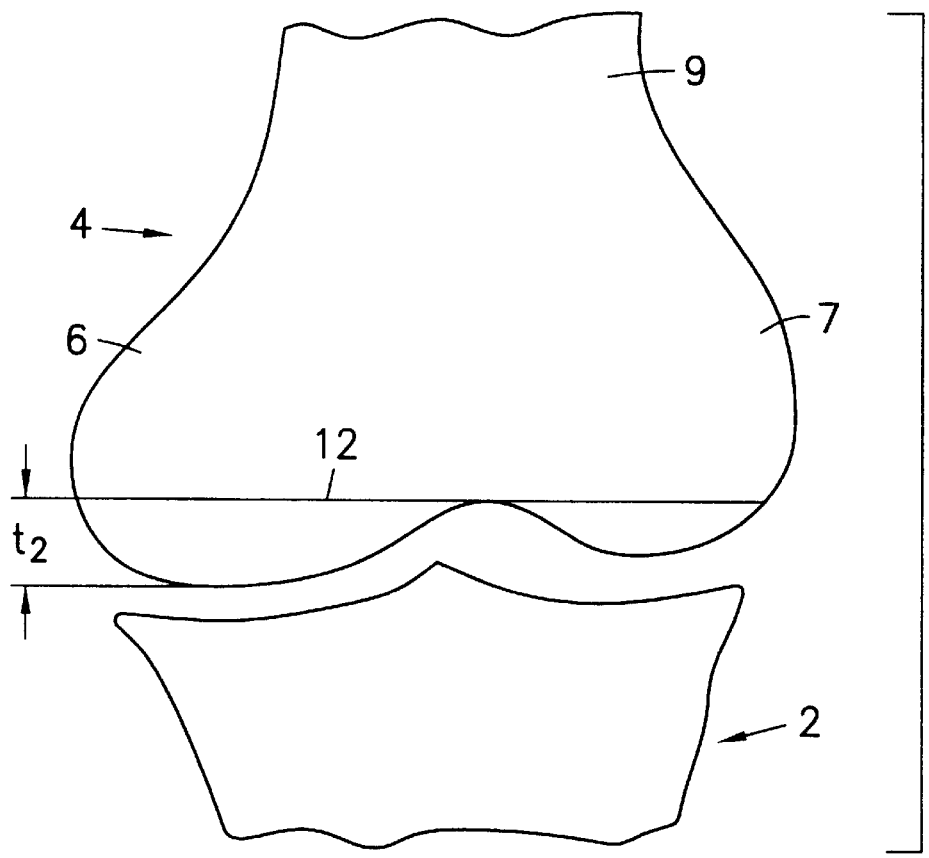
FIG. 2 is a diagrammatic illustration of the knee joint of FIG. 1 seen anteriorly of the joint.

In operation, the femur 1 is rotated 90° from the position shown in FIG. 2 to the position in FIG. 3 or 5 so that the distal end of the femur 1 is exposed. The bore 21 is formed in the femur 1 and the rod 20 is inserted into the bore 21. The tool 30 is then installed in the rod 20 by fitting the bore 32 in sleeve 31 on the stub 24 of the rod 20 projecting from the distal end of the femur 1. The posterior caliper feelers 47 are respectively brought into contact with the posterior surfaces of the respective medial and lateral condyles. This effectively establishes the position of plane T as described in FIG. 3.

Figure 9:
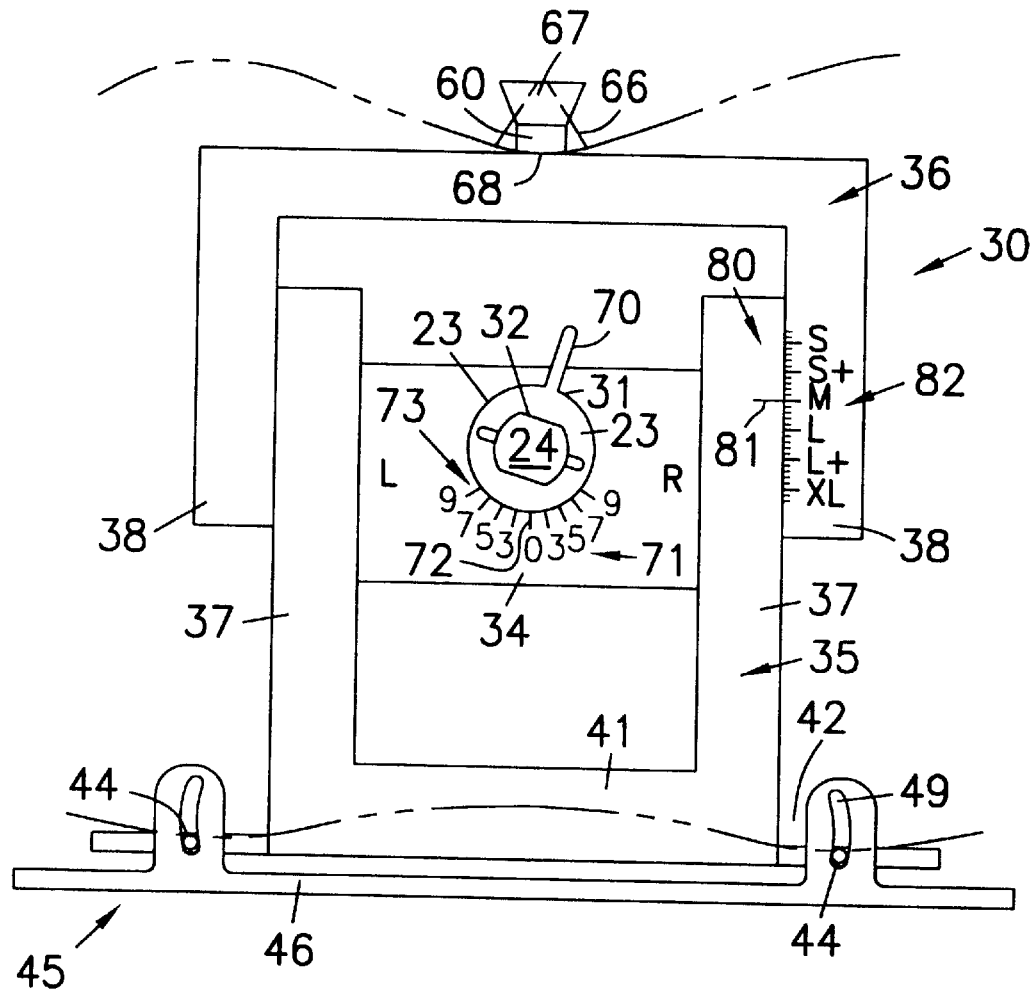
FIG. 9 is similar to FIG. 6 and illustrates a first stage in which the rod is angularly rotated by a specific amount.
Figure 27:
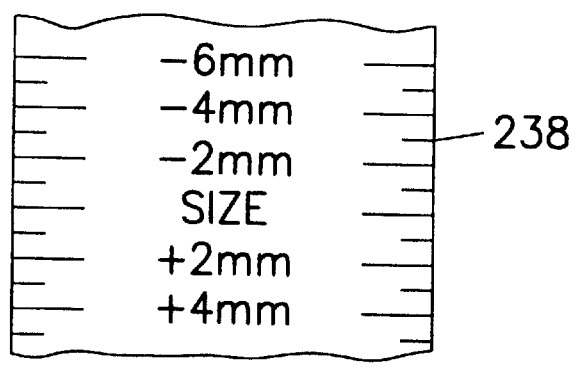
FIG. 27 is an enlarged fragmentary view of the sliding scale of the distal cutting block.

A radially projecting tab 70 on the sleeve 31 is manually engaged to rotate the sleeve 31 through angle A representing the angle determined by the surgeon as explained previously. A scale 71 is provided to indicate the angle through which the sleeve 31, and thereby the rod 20, has been turned. The scale 71 comprises an index marker 72 on the sleeve and an angle scale 73 on the slider 34. The scale 73 is marked for left and right femurs. For left femurs (described and illustrated in the drawing) the sleeve and rod are rotated to the right (clockwise) whereas when the tool is mounted on a rod in the right femur, the sleeve and rod are rotated to the left (counter clockwise). When the scale 71 indicates the desired angle of rotation, the sleeve 31 is rotatably locked in the slider 34 by suitable means (not shown) and the rod 20 is driven into the bore 21 of the femur 1 to be angularly secured thereon in the desired rotational position relative to the plane T tangential to the posterior surfaces of the medial and lateral condyles. This is the position shown in FIG. 9.

Figure 10:
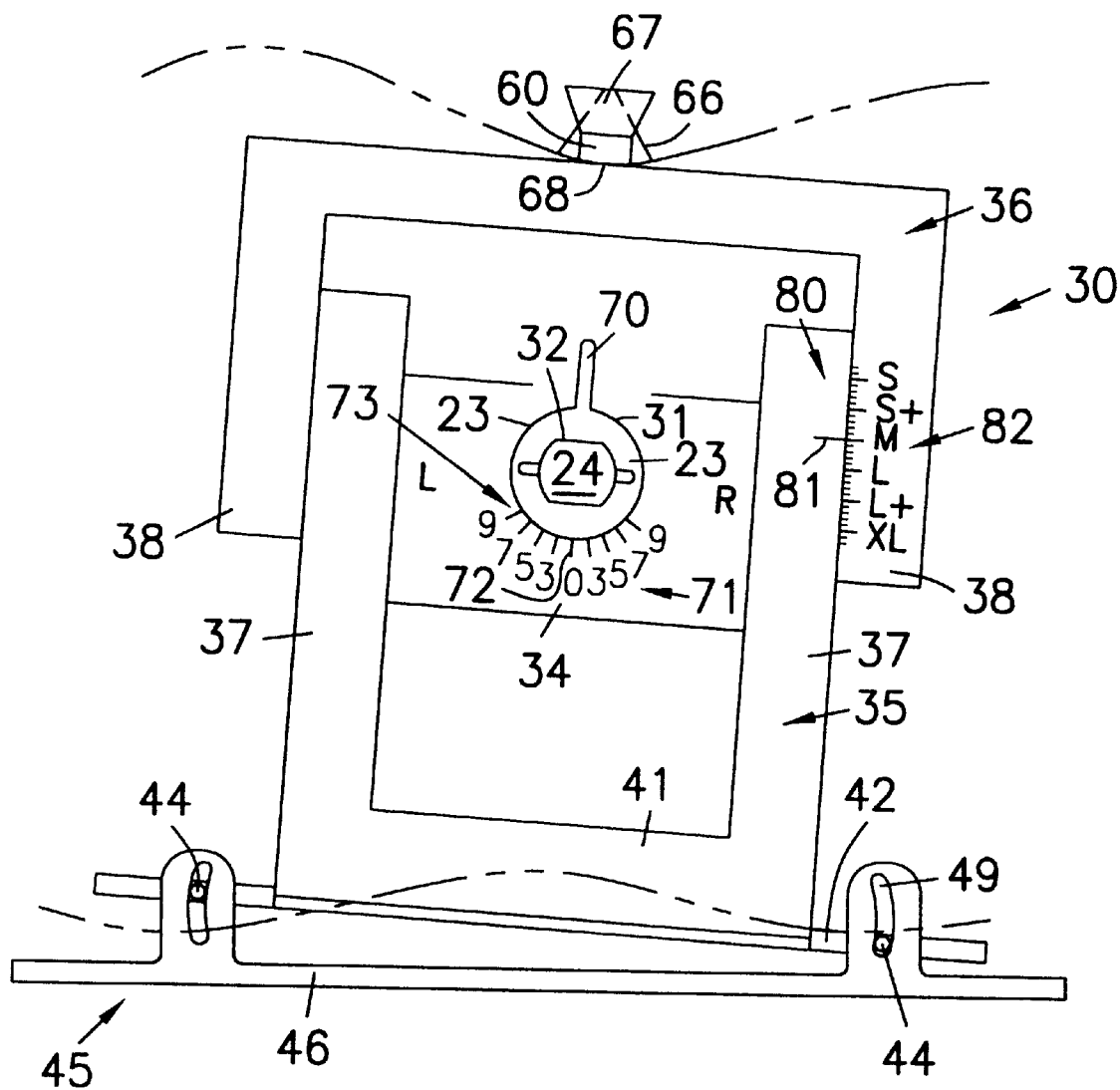
FIG. 10 is similar to FIG. 9 in a subsequent stage.
Figure 11:
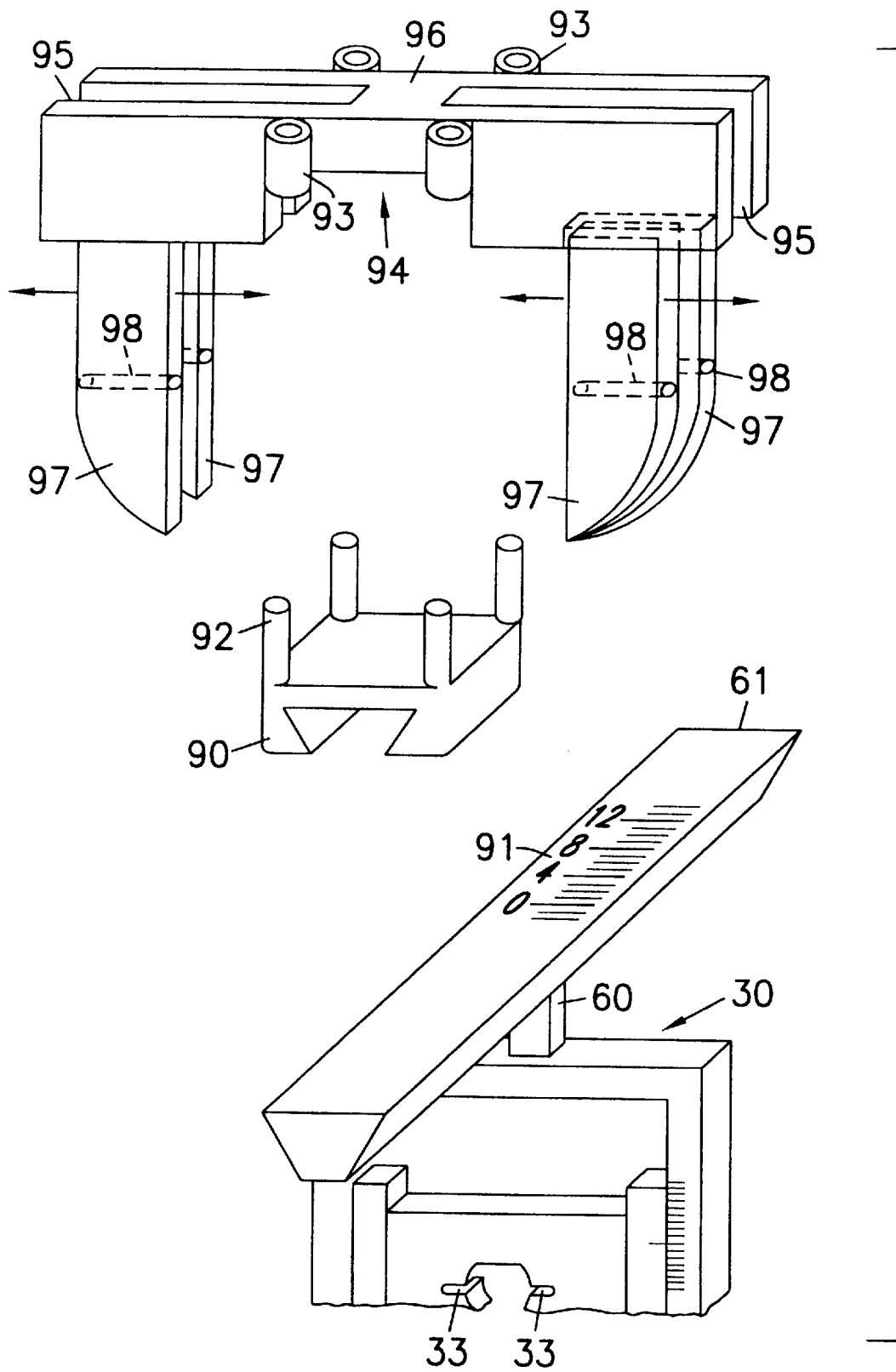
FIG. 11 is an exploded view showing a cutting guide to be installed on the tool.
Figure 12:
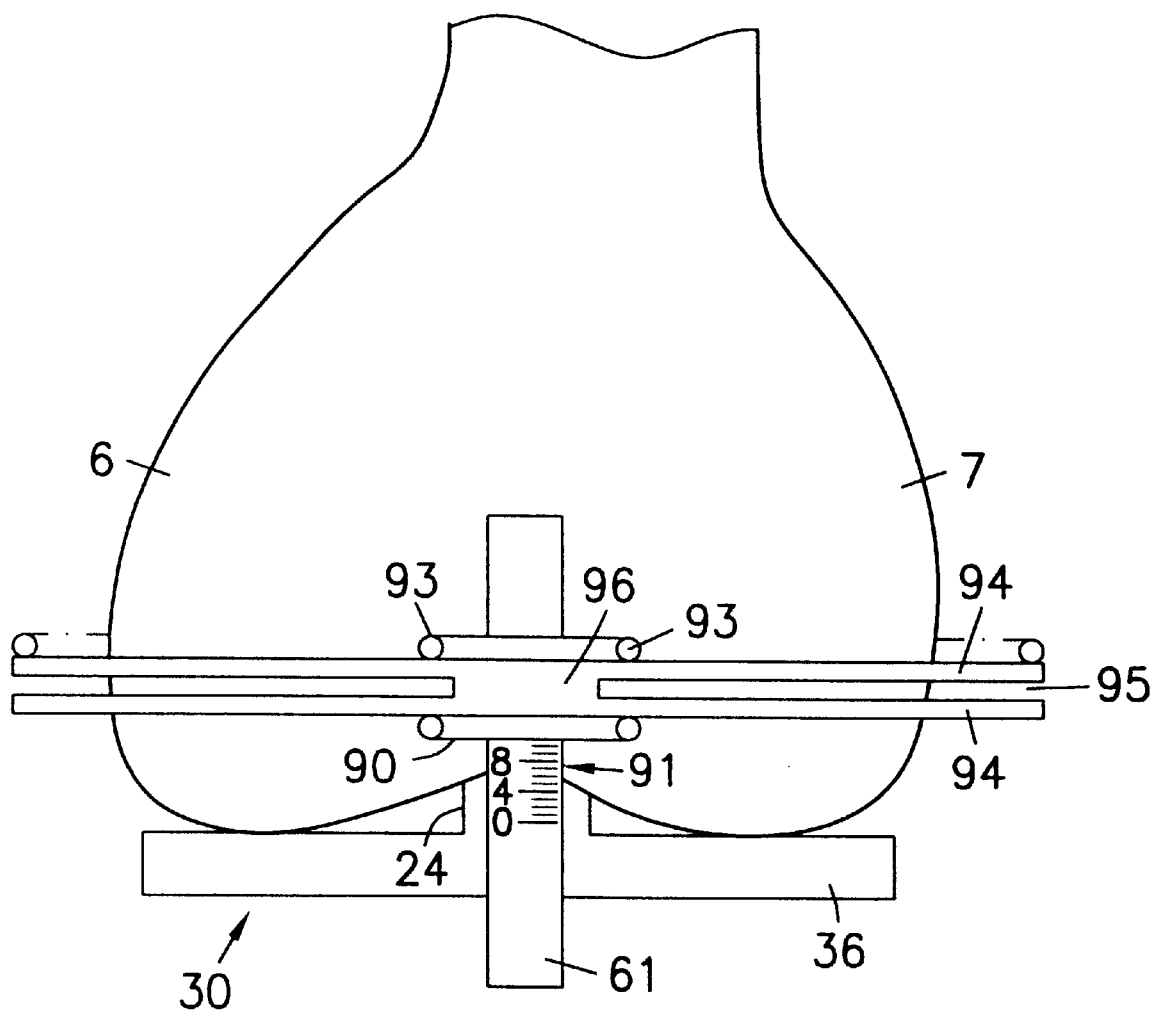
FIG. 12 is a top, plan view showing the cutting guide installed on the tool.

In order to set the caliper means in position to measure the distance D', the nuts 50 on pins 44 are loosened and the upper and lower caliper halves 36 and 37 are rotated as a unit around pin 44 at the lateral femoral condyle until the index marker 72 returns to its zero setting on the scale 73 as shown in FIG. 10. The nuts 50 are then tightened and the caliper halves are now in a position to measure distances perpendicular to the plane P tangent to the posterior surface of the lateral condyle. The capability of slidable movement of the slider 34 on the lower caliper half 35 and of the caliper half 35 relative to bar 42 and posterior caliper feeler 45 permits the rotation of the caliper halves about pin 44 at the lateral condyle while the sleeve 31 and the slider 34 are engaged with the stub 24 of rod 20.

The anterior feeler 64 is then positioned so that sector plate 66 contacts the anterior surface 13 of the femoral cortex. A distance scale 80 is provided between the upper and lower caliper halves 36, 35 and comprises a marker 81 on leg 37 and a scale 82 on leg 38. The scale 82 indicates the prosthesis size and hence is a measure of the distance D. The calibration is such that when the marker 81 is in correspondence with a mark on scale 82 for a particular prosthesis, when this prosthesis is utilized, the difference between D and D' (the thickness $t_3$ resected at the posterior condyle) will be substantially equal to the thickness of the prosthesis to be inserted. If the scale falls between prosthesis markings on scale 82, generally the smaller prosthesis is selected and the resected thickness of the lateral condyle will be slightly increased accordingly. The scale markings can also be calibrated with reference to the resected thickness $t_1$ at the medial condyle to reflect the normally greater thickness resected thereat.

With the tool still mounted on the rod 20, the anterior feeler 64 is removed and a guide 90 is slidably fitted on guide bar 61. At the top of the guide bar 61 another scale 91 is provided. The scale 91 is marked in millimeters and represents the distance from a plane perpendicular to the rod and tangent to the high point of the distal end surface of the more prominent of the medial or lateral condyles. In other words, when the tool 30 remains on the rod 20 and is brought into abutment with the condyles, this is the zero position of the scale 91. The guide 90 has four upstanding pegs 92 which fit into four holes 93 of a distal end cutting guide 94.

The cutting guide 94 is provided with slots 95 extending in a plane substantially perpendicular to the axis of stub 24. The slots 95 extend from the medial and lateral side surfaces of the cutting guide 94 towards the center thereof. The slots 95 are adapted to guide a narrow cutting blade (not shown) for respectively cutting the medial and lateral condyles 6, 7 along planar cut 12. The slots 95 are separated by a solid, intermediate section 96.

The position of the slots 95 relative to the scale indicate the thickness $t_2$ to be resected by the planar cut 12 at the distal end of the femur 1. The invention contemplates that the thickness $t_2$ may be equal to the thickness $t_3$ determined by the measurement of distance D'. Therefore, the guide 90 is moved until the slots 95 are aligned with the distance on scale 91 equal to the determined thickness $t_3$. The guide 90 is then locked on guide bar 61 by suitable means (not shown).

Depending feet 97 are slidably mounted on cutting guide 94 in respective pairs on opposite sides of each slot 95. After the cutting guide 94 has been moved to its cutting position as indicated on scale 91, the depending feet 97 are slidably moved to abut against respective portions of the condyles. The feet 97 are provided with nail holes 98 and nails (not shown) are driven into the holes 98 to secure the cutting guide 94 to the femur 1. A conventional cutting blade is then inserted in guide slots 95 to cut the distal ends of the condyles 6, 7 along the planar cut 12. The feet 97 nailed to the condyles prevent skewing or sliding of the cutting guide during the cutting operation.

Figure 13:
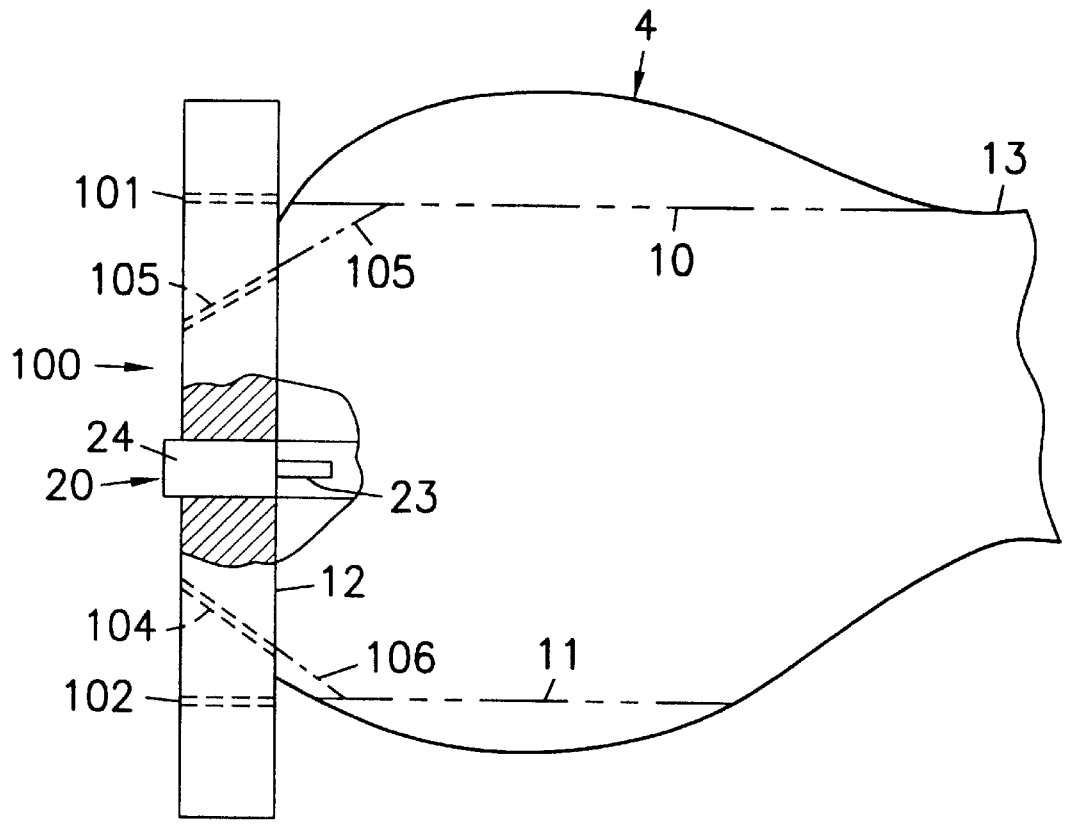
FIG. 13 illustrates the distal end of the femur after the distal end has been cut and an AP cutting guide has been placed on the rod.
Figure 24:
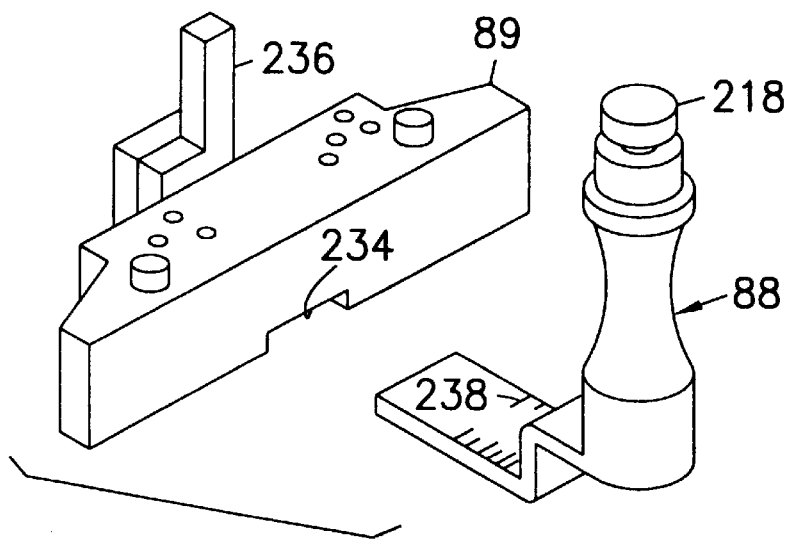
FIG. 24 is an exploded view of a distal cutting block to be installed on the tool of FIG. 21.

The tool 30 is then removed from the rod 20 and a conventional AP cutting guide 100 (FIG. 13) is fitted on the end of the rod 20 and abutted against the planar surface 12 now cut at the distal end of the femur 1. The cutting guide 100 is provided with guide slots 101 and 102 which can be precisely placed for guiding a cutting blade to produce the anterior and posterior cuts 10, 11 respectively. The cut 10 will be flush with anterior surface 13 of the femoral cortex and the cut 11 will be at distance D therefrom. The AP cutting guide 100 also includes angular slots 103, 104 to form chamfer cuts 105, 106 on the femur 1 which match corresponding angular surfaces 107, 108 on the knee prosthesis 5.

Figure 14:
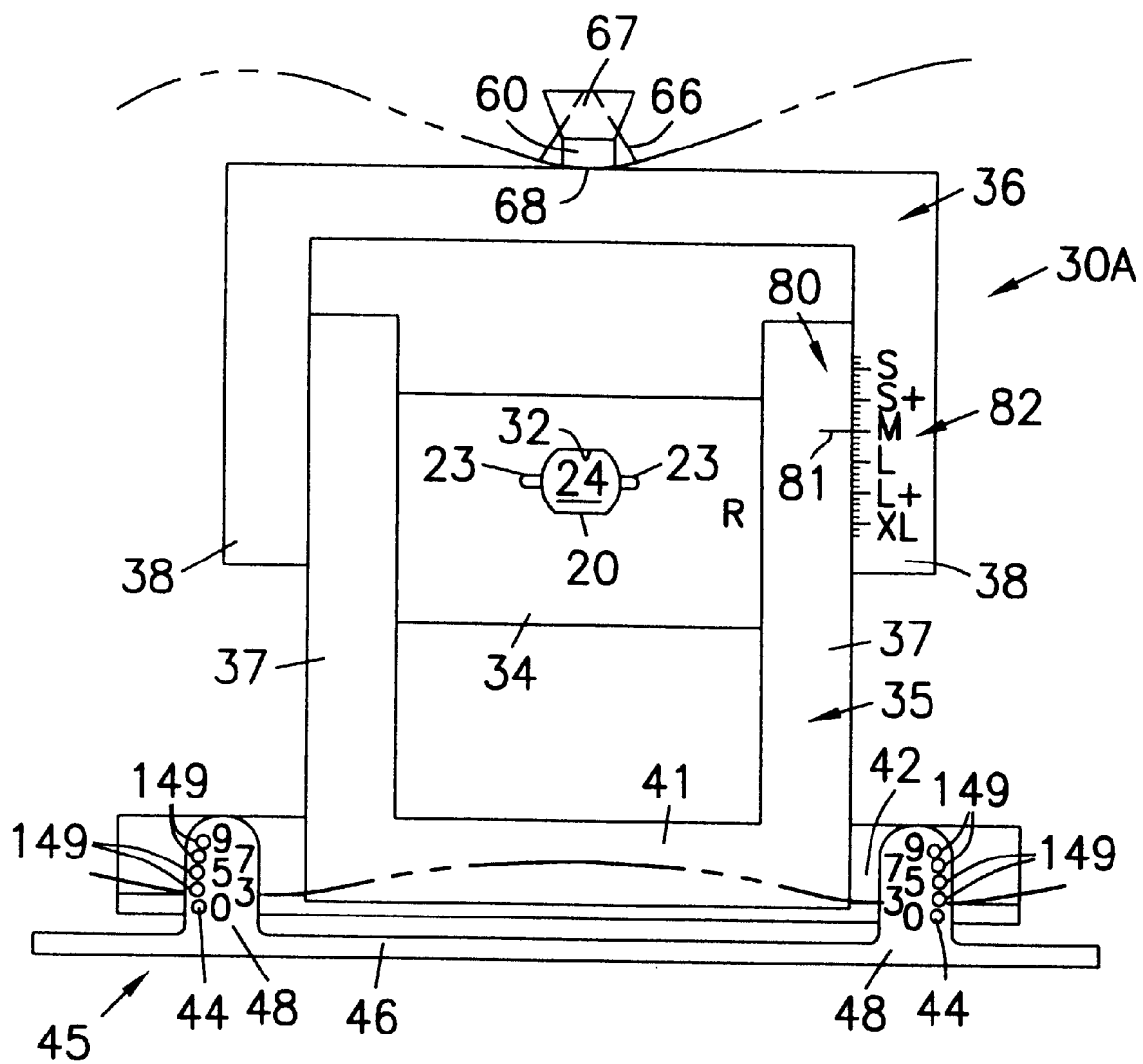
FIG. 14 is an end view similar to FIG. 6 of a second embodiment of the tool.
Figure 15:
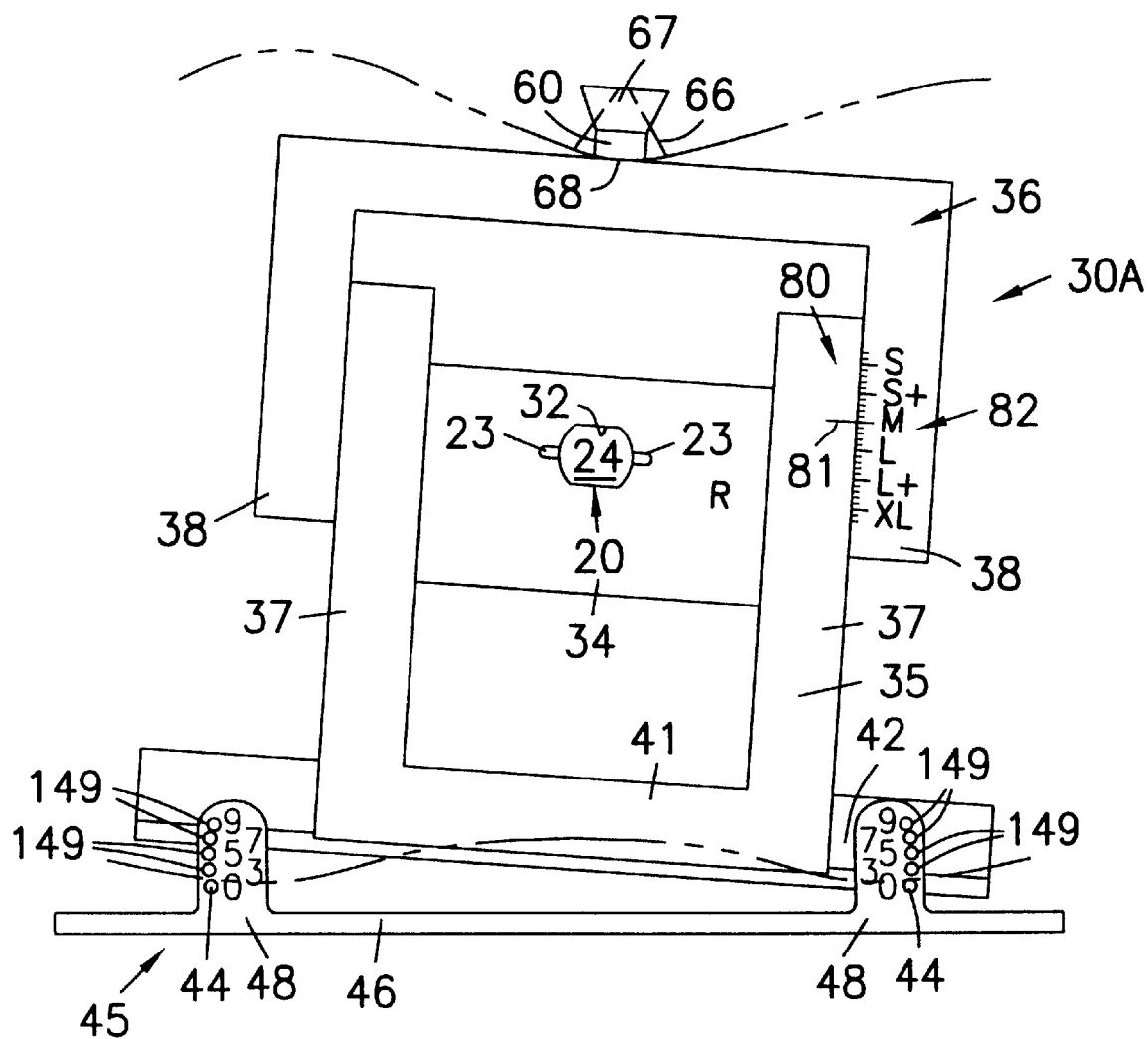
FIG. 15 shows the tool of FIG. 14 in a rotated state.

FIGS. 14 and 15 illustrate a second embodiment of a tool 30A which is a simpler version of the first embodiment of FIGS. 5–10 and wherein the same reference characters are used to designate like elements.

Essentially, the embodiment of the tool 30A of FIGS. 14 and 15 differs from that of FIGS. 5–10 in eliminating the rotatable sleeve 31 and directly engaging the stub 24 of rod 20 in bore 32 now provided directly in the slider 34. The slider 34 thus serves as the engaging means for the stub 24. The legs 48 on the caliper plate 46 are provided with spaced holes 149 instead of the continuous slot 49 of the embodiment of FIGS. 5–10 and angular markings 173 are provided adjacent to the holes 149 to indicate the magnitude of angle A between the caliper plate 46 and bar 42, serving as a measurement plate, when the pin 44 is in the respective hole 149. In the illustrated embodiment in FIGS. 14 and 15, the holes 149 are placed to provide angulations of 0, 3, 5, 7 and 9° left and right between bar 42 and caliper plate 46.

In operation, the stub 24 is engaged in the bore 32 in slider 34 and pins 44 are placed in the 0° holes in respective legs 48. The caliper feelers 47 are placed into tangential contact with the posterior surfaces of the medial and lateral condyles 6, 7 respectively. The pin 44 in the leg 48 corresponding to the medial condyle is then removed from the 0° hole and placed in the hole 149 corresponding to the desired angulation of the rod 20. This is shown in FIG. 15 where pin 44 is set in the hole 149 to angulate the bar 42, 70 relative to the caliper plate 46 and thereby relative to the plane T tangent to the medial and lateral condyles. By virtue of the slidable supported of slider 34 in legs 37 and the slidable support of cross leg 41 on bar 42, the tool 30A is capable of remaining in position on stub 24 and rotating around pin 44 at the posterior surface of the lateral condyle 7.

The measurement by the caliper means to determine the size of the prosthesis and the resected thickness $t_3$ at the lateral condyle is carried out in the same way as in the first embodiment and the planar cuts are then made on the condyles as previously described.

As was described for the first embodiment of tool 30, it is also possible to effect measurement with the tool 30A to determine thickness $t_1$ at the medial condyles and to utilize this thickness to establish the thickness $t_2$ distal cut 12.

Both the first and second embodiments have been described with regard to the intramedullary rod 20 with radial flutes 23 to embed the rod securely in the bore 21 in the femur 1 to establish the datum or benchmark position for attaching the cutting guide 60 to effect the distal end cut 12 and thereafter the AP cutting guide 100 to effect the anterior and posterior planar cuts 10, 11. However, other suitable means can be employed to secure the angular position of the rod instead of the flutes 23. Moreover, since the rod 20 is ultimately removed from the femur 1 after the planar cuts 10, 11, 12 have been made, the absence of the flutes 23 makes removal simpler.

Figure 16:
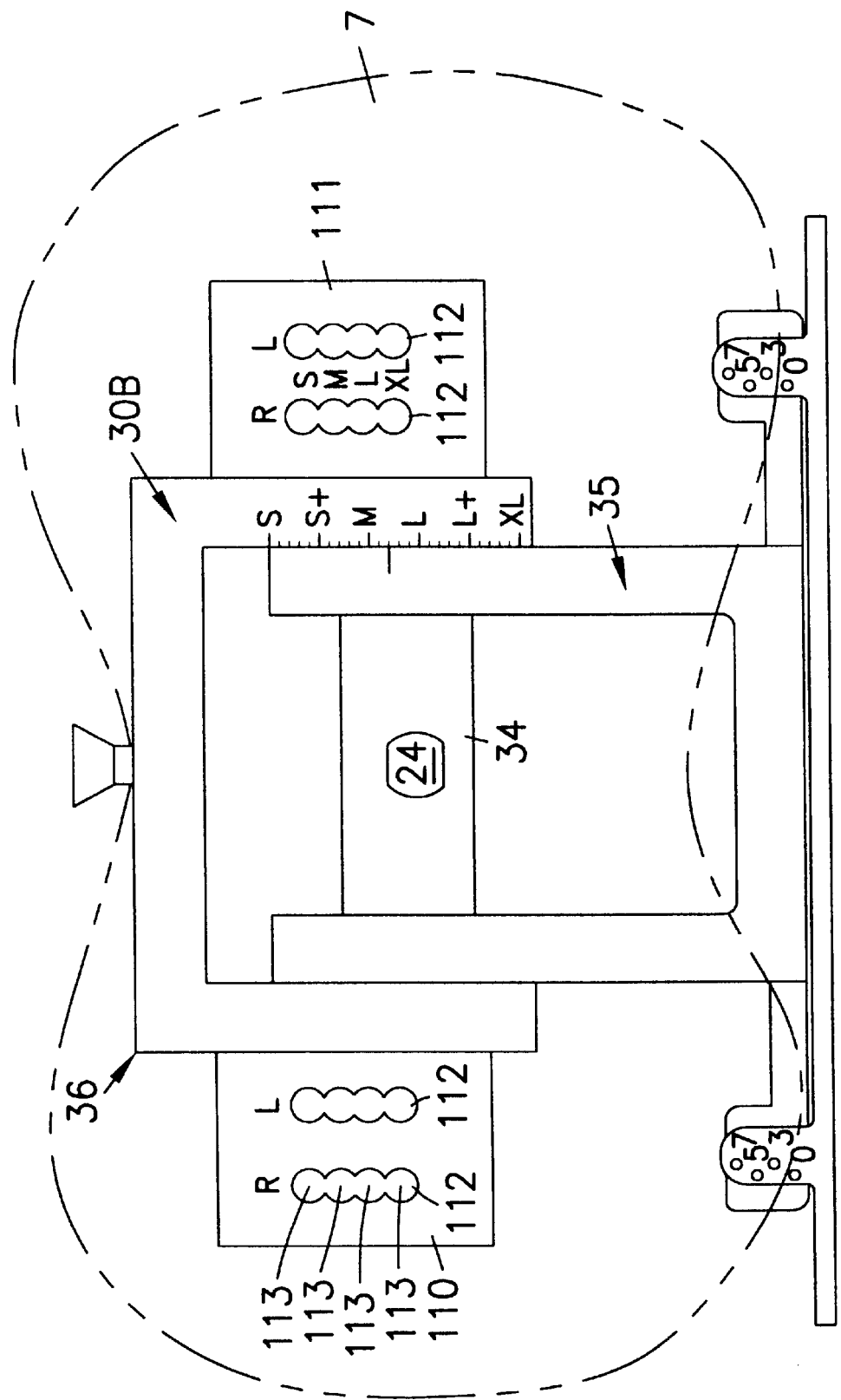
FIG. 16 is an end view similar to FIG. 6 of a third embodiment of the tool.
Figure 17:
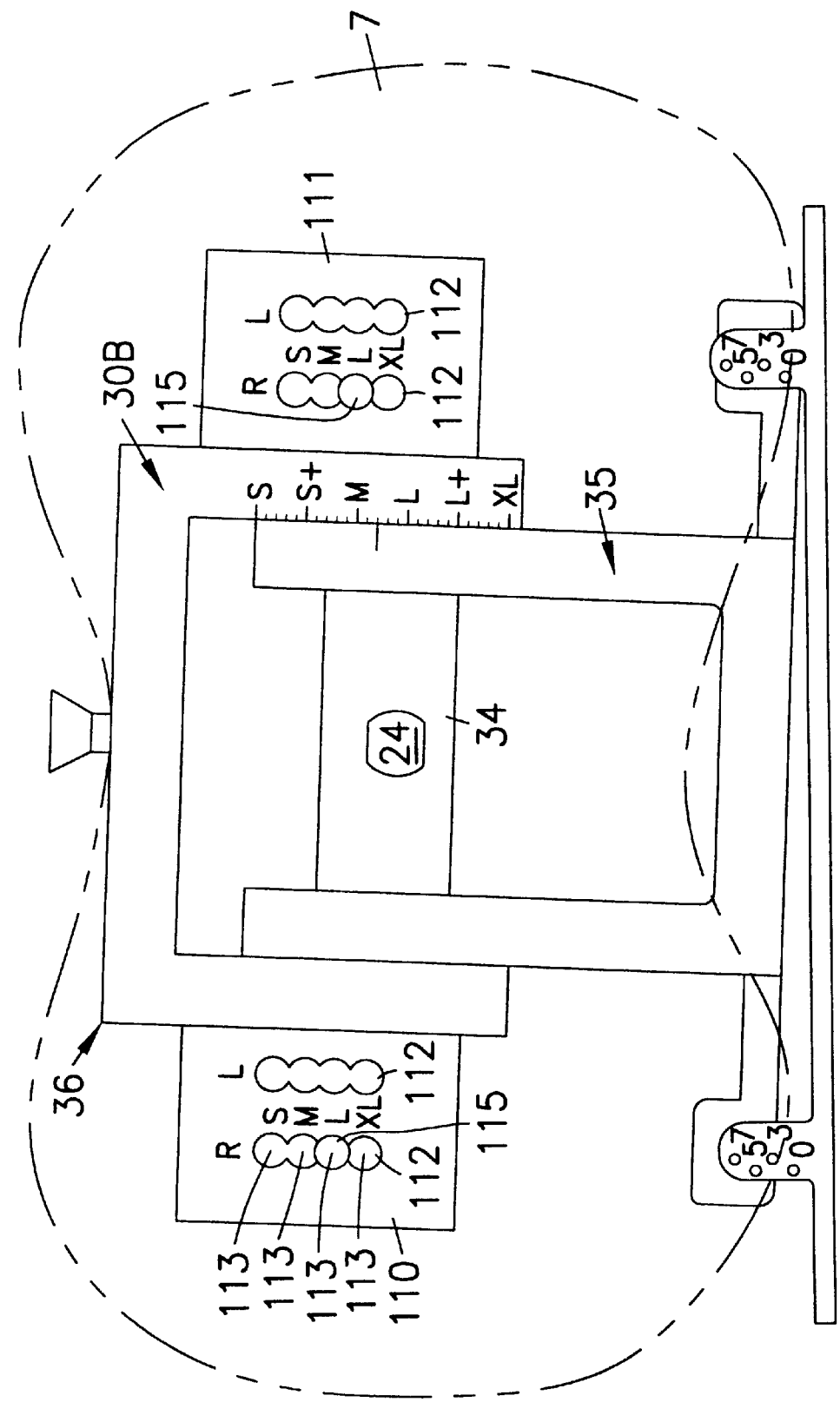
FIG. 17 shows the tool of FIG. 16 in a rotated state.

FIGS. 16 and 17 illustrate a third modified embodiment of the tool 30B which secures the angular datum position by use of a rod without flutes 23. The same reference characters as in the first two embodiments designate like elements.

In the third embodiment, the rod 20 is smooth and devoid of flutes 23. The rod 20 is rotated to its adjusted angular position, as in the first and second embodiments, and in order to secure an angularly adjusted datum position, lateral plates 110, 111 are secured to the legs 38 of the upper caliper half 36. Each plate 110, 111 contains two vertical rows 112 of overlapped holes 113. The rows 112 are designated for right and left femurs and the holes 113 are respectively graduated in size order from the scale 82. When the caliper means of the tool 30B has been rotated to the desired degree of angulation, pins 115 or similar fasteners are placed in the appropriate holes 113 in the lateral plates 110, 111 and secured in the distal ends of the medial and lateral condyles so that the pins 115 project from the distal ends of the condyles. The pins 115 establish an angular datum position representing the rotation of the tool. The steps of measurement of prosthesis size, and of effecting the planar cut with the guide 60 are carried out as in the previously described embodiments. However, after the distal end cut 12 is made, the tool 30B is removed leaving the pins 115 in place in the condyles, the rod 20 is removed from the femur 1, and a guide 100' is mounted on the pins 115 which serve to accurately position the guide 100' so that the slots 101–104 will be precisely located for exact placement of the cuts 10, 11, 105 and 106. The guide 100' has holes 116 to receive the pins 115 which are precisely located with regard to the slots 101–104 to insure accurate location of the cuts when the guide 100' is mounted on the pins 115. After the cuts have been made, the pins 115 are removed from the condyles. As evident from the above, the embodiment contemplates the use of the pins 115 as the means to provide the datum position for the cutting guide 100' in lieu of the rod 20. The use of the plates 110, 111 and of the pins 115 is applicable to the other embodiments as well.

Figure 18:
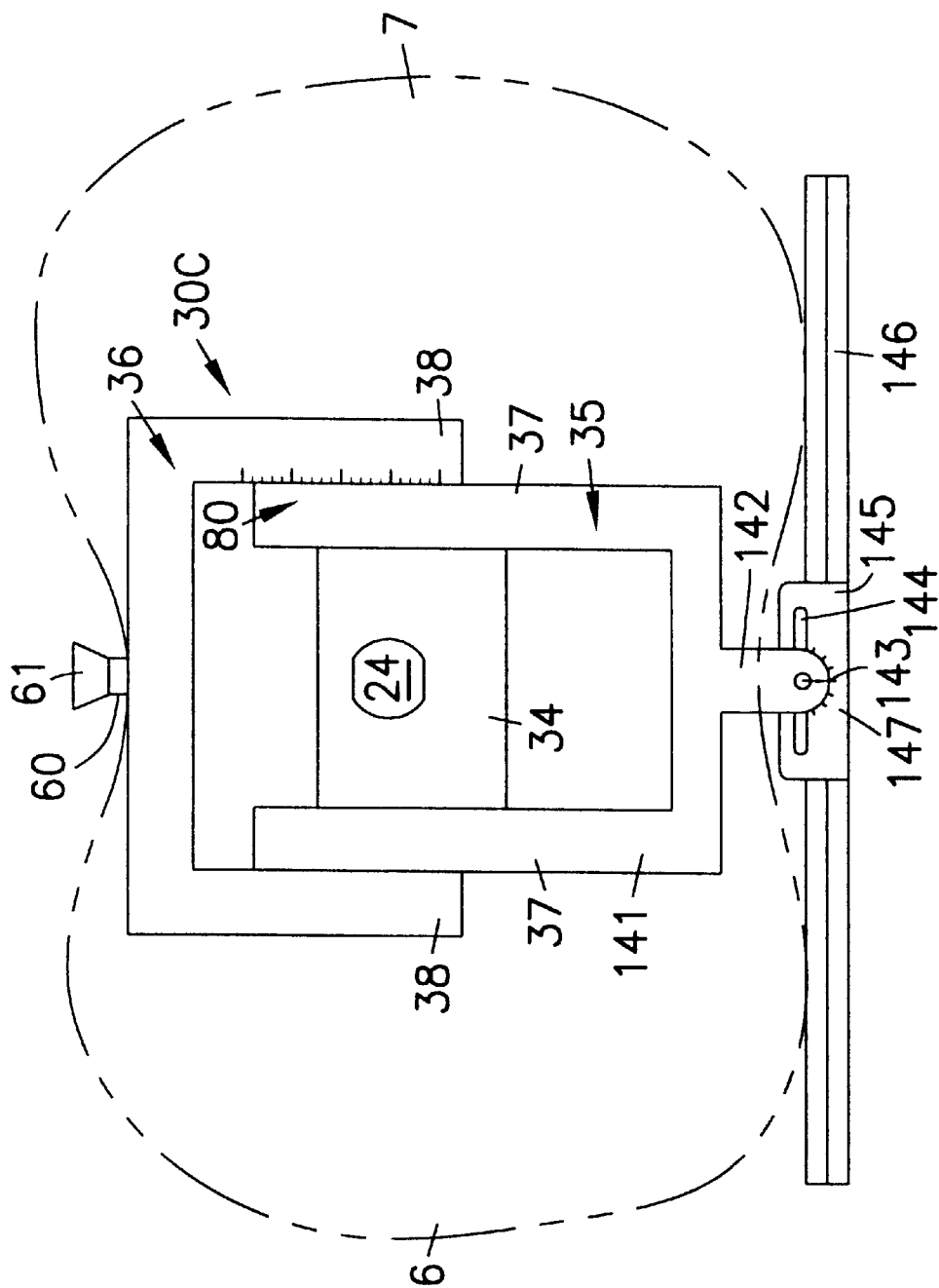
FIG. 18 is an end view similar to FIG. 6 of a fourth embodiment of the tool.
Figure 19:
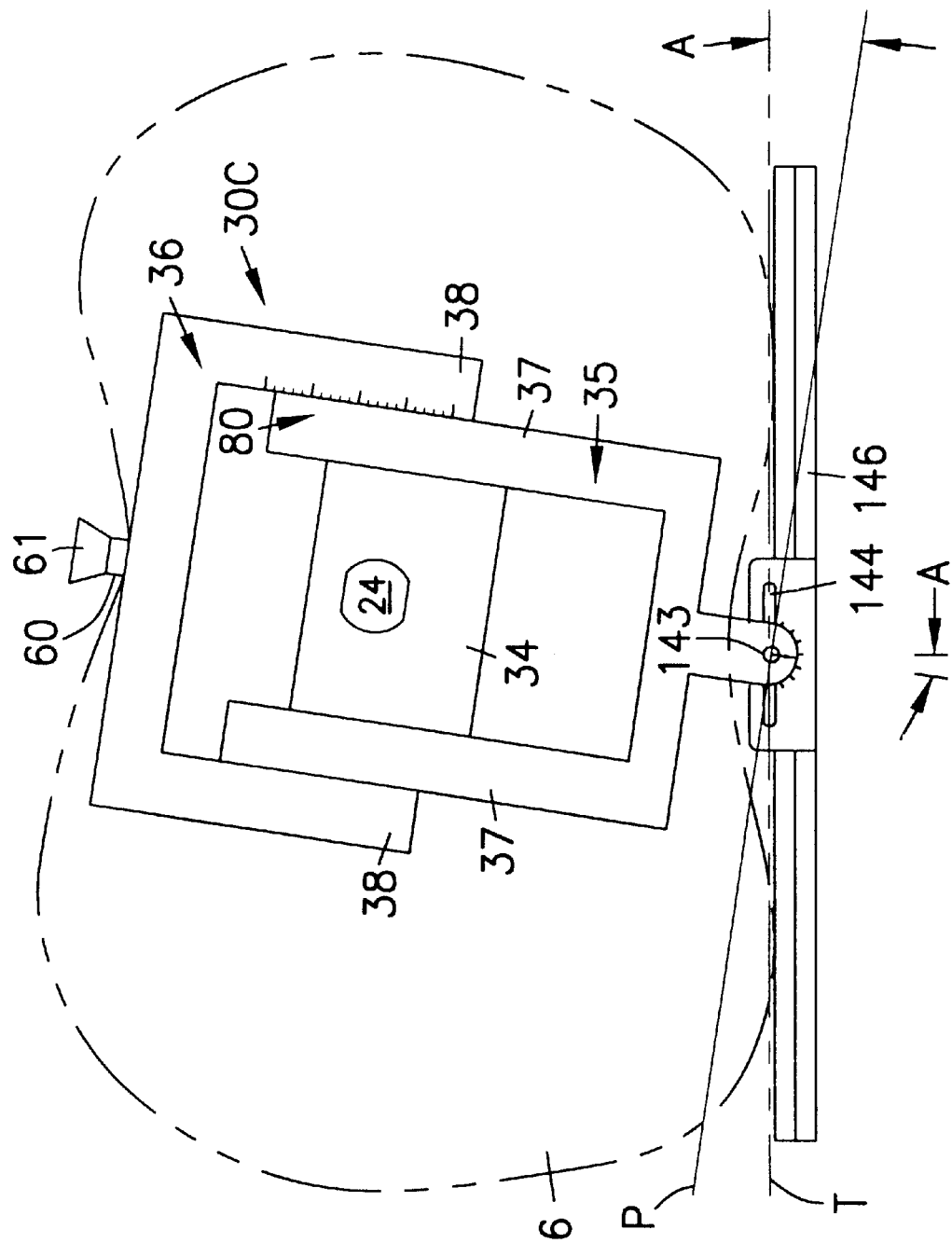
FIG. 19 shows the tool of FIG. 18 in a rotated state.
Figure 20:
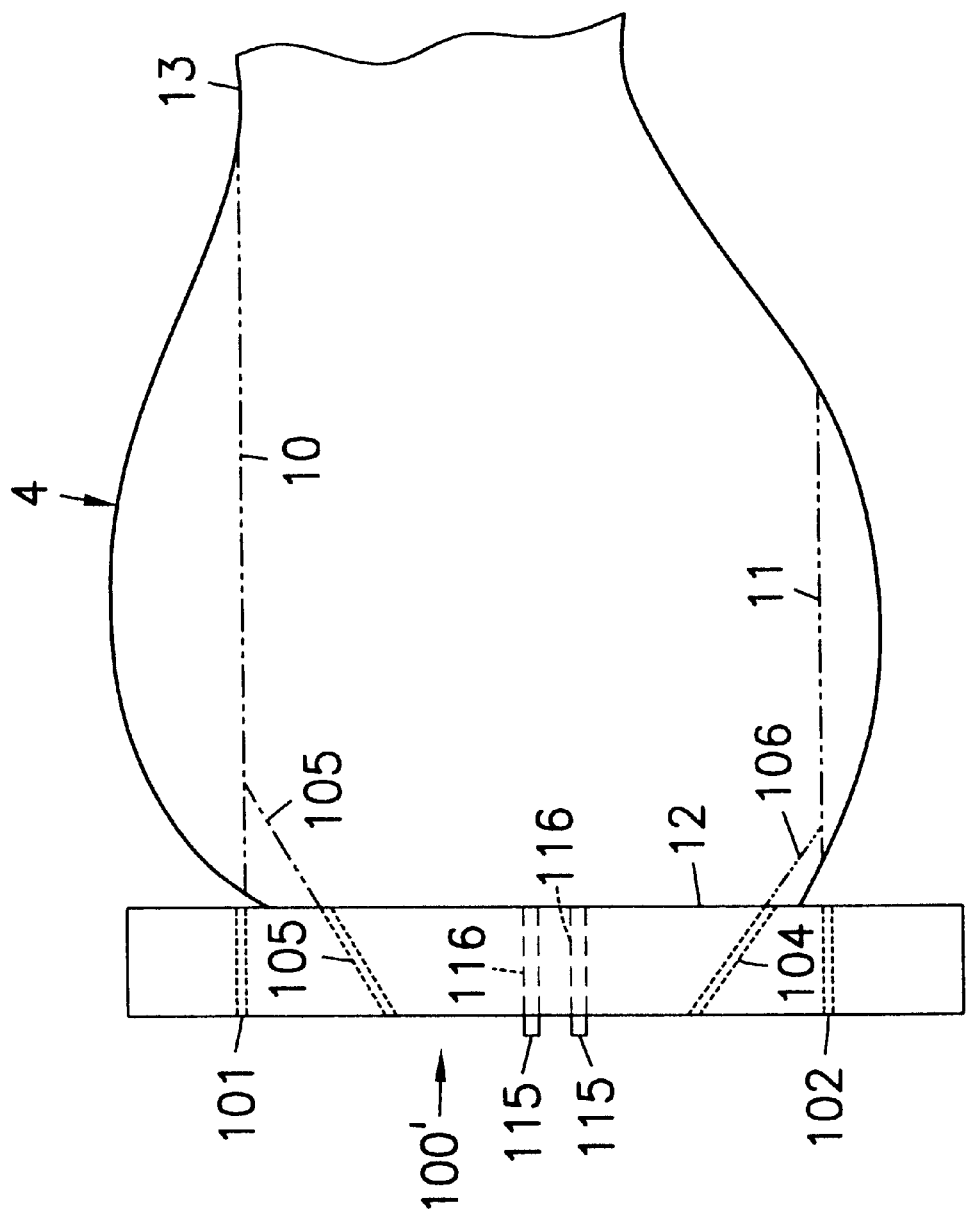
FIG. 20 is similar to FIG. 13 but shows a modification adapted to the embodiment of FIGS. 16 and 17.
Figure 21:
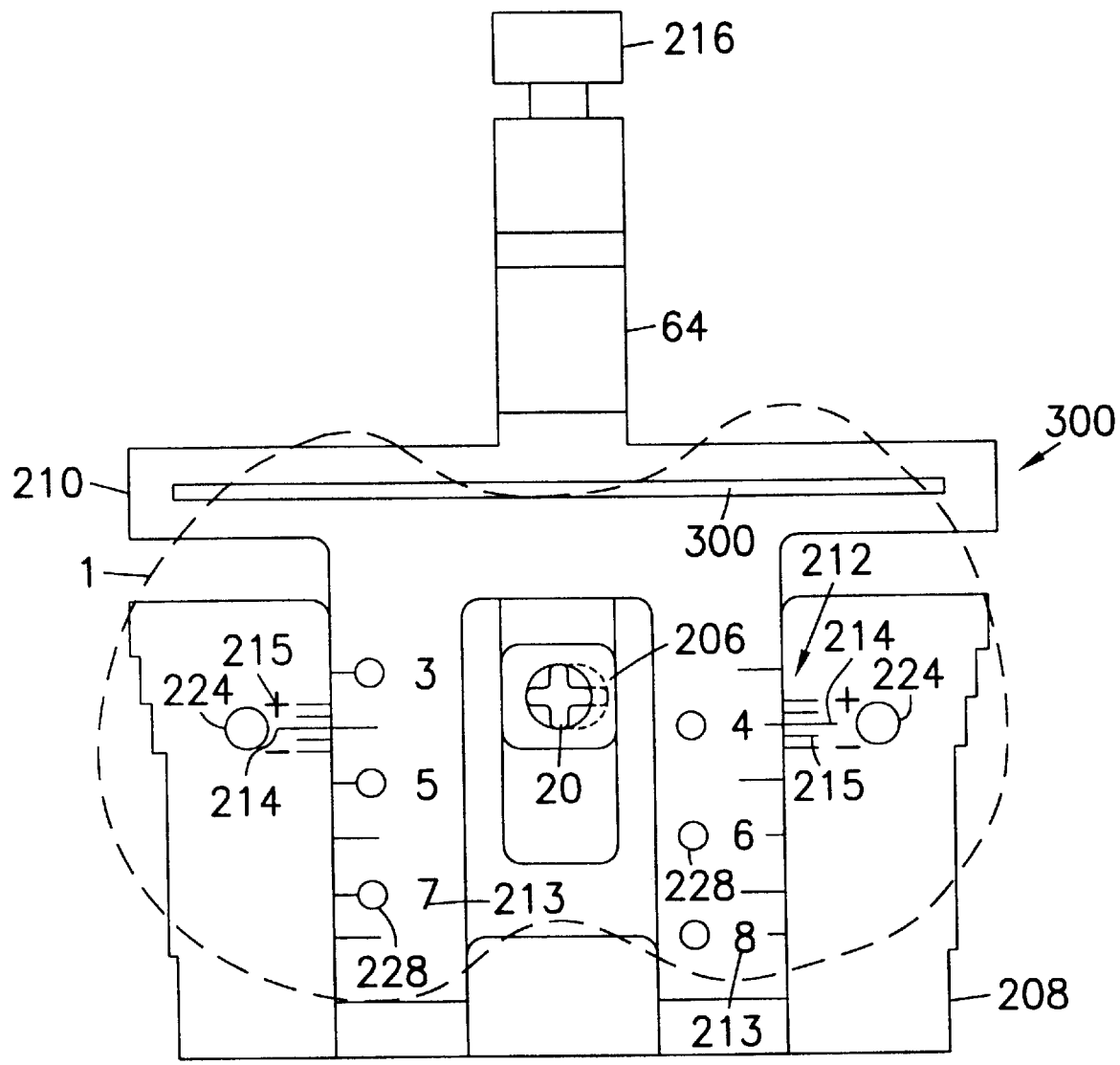
FIG. 21 is an end view similar to FIG. 6 of a fifth embodiment of the tool including an A-P measuring guide.

FIGS. 18 and 19 illustrate a fourth modified embodiment of the tool 30C which is a simplified version of the second embodiment of FIG. 14 and uses the same reference characters to designate like elements.

The tool 30C utilizes slider 34 which engages the rod end 24 and is slidably engaged in the legs 37 of the lower caliper half 35. The legs 37 of the lower caliper half 35 are slidably engaged with the legs 38 of the upper caliper half 36.

At its lower end, the lower caliper half 35 includes a cross bar 141 from which a leg 142 depends. The left 142 supports a pivot 143 which slidably rides in a slot 144 in a bracket 145 integral with posterior caliper plate 146. The posterior caliper plate 146 is similar to caliper plate 46 of the second embodiment and includes posterior caliper feelers for contacting the medial and lateral condyles 6 and 7. The slot 144 extends substantially parallel to the caliper plate 146 in the plane of tangential contact of the posterior feelers with the posterior surfaces of the medial and lateral condyles. An angle scale 147 is provided between the leg 142 and the bracket 145.

In the initial position of the tool, the slider 34 is fitted on the end 24 of the rod and the posterior feelers are brought into tangential contact with the medial and lateral condyles. The caliper means 35, 36 are rotated, while the rod 24 is held fixed, until the angle scale 147 reads zero. The pivot 143 is disposed in the slot 144 substantially in the plane T tangent to the posterior surfaces of the medial and lateral condyles. The tool 30C is then rotated to cause the end 24 to rotate through an angle A corresponding to the determined angle of rotation. The angle A is read on the angle scale 147. The pin 143 undergoes slidably movement in slot 144 while the slider 34 undergoes slidable movement in lower caliper half 35 to accommodate the rotation of the tool. The pin 144 remains in the tangential plane T. The scale 80 is a measure of the distance from the anterior feeler in contact with the anterior femoral cortex and the pin 143 along a perpendicular line from the anterior femoral cortex to a plane P passing through the pin 144 and inclined relative to posterior caliper plate 146 by the angle of rotation A of the tool. Any difference between the distance from pivot point 67 to the surface 68 of the sector plate 66 and the corresponding distance measured along the perpendicular to the incline plane P is negligible and even for an angle A of 12° the difference will be less than one-third mm.

As an alternative to the slot 144, the bracket 145 can be provided with a series of holes representing different angles of the caliper means 35, 36 relative to the plate 146, corresponding to different angles A, as in FIG. 14. The holes are provided along the axis of slot 144 in order to be in tangential plane T of the posterior feelers on the posterior surfaces of the condyles. When the pin 143 is secured in a respective hole the caliper means is secured at the angle designated by the associated hole. In the use of this alternative, with the tool not yet fitted on the end 24, the angle of the caliper means is set by inserting the pin 143 into the selected hole and the posterior feelers on plate 146 are brought into tangential contact with the condyles 6, 7. The tool is then fitted on the end 24 which now assumes the angle of the caliper means relative to the plate 146. The rod 20 is then driven into the femur 1 as before, or alternatively, as in the embodiment of FIGS. 16 and 17, pins 115 are installed in the condyles through holes in plates 110, 111 installed on the upper caliper half of the tool. The subsequent operations are the same as previously described.

FIGS. 21–33 illustrate a fifth modified embodiment of a tool 30D which is a simplified version of the first four embodiments of FIGS. 1–20 and wherein like reference characters are used to designate like elements. The tool 30D is specially adapted to be used in connection with a GENESIS II Total Knee System supplied by Smith & Nephew Richards, Inc. of Memphis, Tenn. It should be realized, however, that the tool 30D can be adapted to be used with knee systems of other manufacturers.

Figure 33:
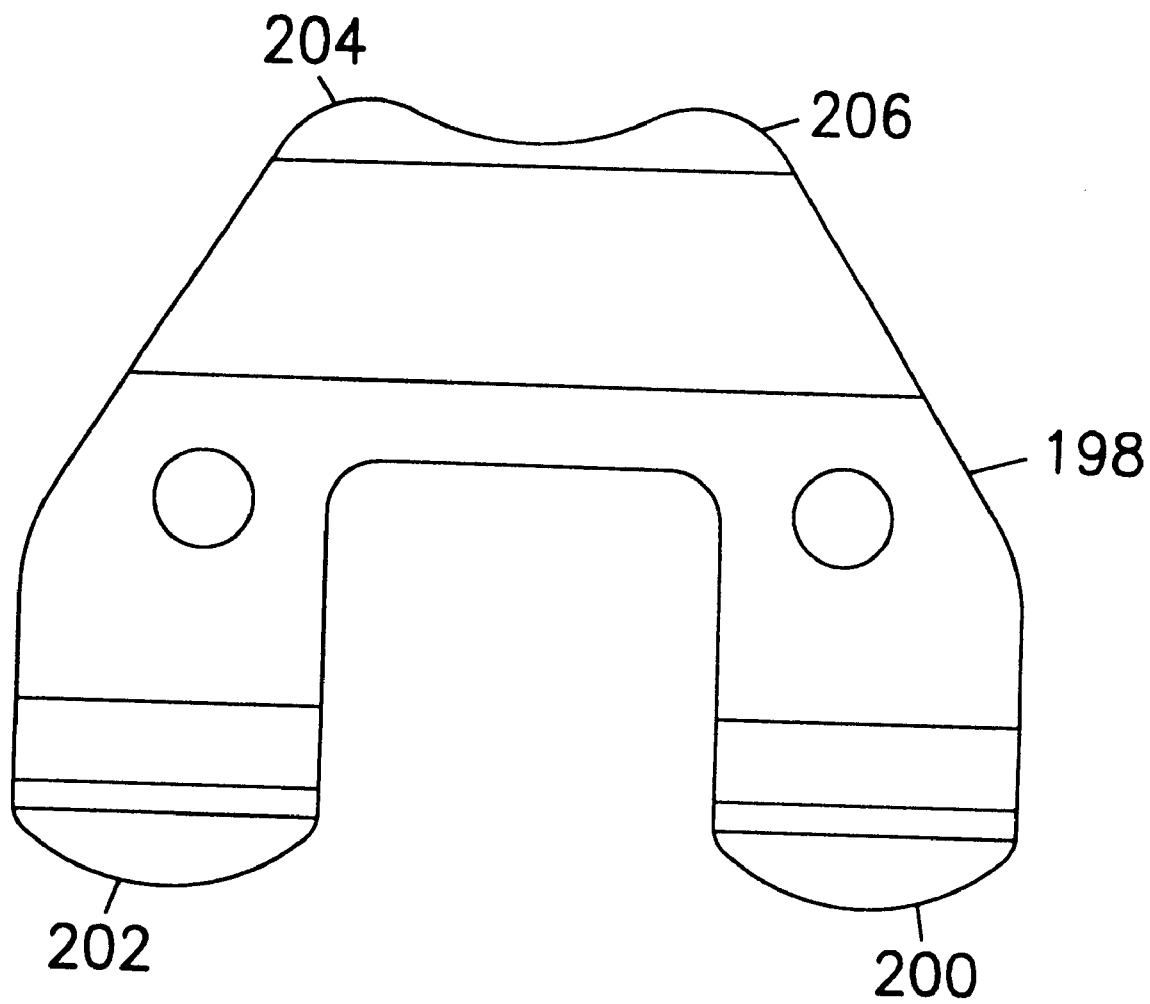
FIG. 33 is a front view of the preferred prosthesis to be used with the tool of FIG. 21.

Referring now to FIG. 33, there is shown a GENESIS II femoral prosthesis 198. The thickness of the distal femoral condyles of the prosthesis is about 9.5 mm (about 9–9.5 mm). The prosthesis 198 has a 3° external rotation or varus angulation built therein. This is accomplished by altering the thickness of the femoral condyles posteriorly. For example, the thickness of the posterior lateral femoral condyle 200 of the prosthesis is about 3 mm thicker (about 2.5–3 mm) than the posterior femoral medial femoral condyle 202. The thickness of the anterior medial femoral condyle 204 and the anterior lateral femoral condyle 206 are about the same. The GENESIS II tibial prosthesis assembly, not shown, has a tibial baseplate (metal) thickness of about 2 mm and a tibial prosthesis (plastic) thickness of about 7.5 mm.

When using the tool 30D and the GENESIS II prosthesis 198, the joint line will be realigned parallel to the floor. This changes a normally 3° varus angle to 0°. A 3° angle amounts to approximately 1.5 mm per linear inch. Assuming the tibiofemoral weight-bearing area is 2 inches apart on average, then 3 mm more laterally than medially must be resected from the tibia to achieve the resection parallel to the floor. To achieve a rectangular flexion and extension space, it follows that 3 mm more from the distal medial femoral condyle than the distal lateral femoral condyle must also be resected.

An objective is to maintain the prosthetic joint line as near anatomic as possible. Assuming the above prosthetic dimensions for the GENESIS II, 8 mm must be resected from the medial tibial condyle or 11 mm from the lateral tibial condyle. This will give a 9.5 mm resection at the midpoint at 0°. With the tibial insert of 9.5 mm replaced, the joint level will be elevated 1.5 mm medially and lowered 1.5 mm laterally, but the patellofemoral joint level will be near anatomic. It follows then that 11 mm from the distal medial femoral condyle and 8 mm from the distal lateral femoral condyle must be resected to achieve the desired 19 mm bony resection to accommodate the 19 mm dimensions of the prosthetic implants.

The surgeon must decide whether to resect the thickness of the combined tibial-femoral prosthesis (i.e., 19 mm) from either the medial or lateral side of the femur 1. The most intact side, least affected or the convex side should be chosen.

When calculating the amount to be resected for the convex side, the surgeon should include an estimate of the "millimeters" of convex ligament laxity. Otherwise, a thicker than necessary tibial prosthesis may be necessary.

Normally the distal femoral resection guide i.e., the lower half 208 of tool 30D (FIG. 21) will contact the medial femoral condyle and be approximately 3 mm off the lateral femoral condyle. In this situation, 11 mm would be resected from the medial femoral condyle. If the knee is in varus and the distal femoral resection guide contacts the lateral femoral condyle, only 8 mm of bone from the lateral femoral condyle must be excised. Therefore, the medial side must be under-resected by 3 mm. Any measurements between these extremes can be easily calculated.

Resecting more than 8 mm medially or 11 mm laterally from the tibial plateau (proximal tibia) may detach or significantly weaken the posterior cruciate ligament ("PCL") insertion more than is compatible with useful function. A tibial plateau that compensates for a lost PCL may be necessary. Also, lowering the tibial resection may place the tibial prosthesis on to a less supportive cancellous surface.

It is important to achieve proper ligament balancing and not equal flexion-extension spacing. The "normal" knee is stable in full extension and has some laxity in flexion. A surgeon should allow an extra 2–3 mm of laxity in flexion to accommodate the normal laxity. If the knee has full unhindered motion, resection in flexion and extension are equal. If flexion is limited, however, an extra few mm in flexion must be resected. (See "Loss of Flexion" situation described below).

A 1 mm resection is approximately equal to 5° increased motion in both flexion and extension. Although this varies slightly from smaller patients to larger patients, the results are relatively consistent. This also implies that if the femur 1 is under-resected distally by 1 mm or over-resected posteriorly by 1 mm, 5° extra flexion should be achieved.

When checking range of motion before closing, at least 10° of laxity is required in flexion and extension. When arthroscoping a knee, initially the joint is quite snug. After "wrestling" with the knee for 5–10 minutes, the joint seems to "loosen up". This can be attributed to "stretching" the ligamentous structures around the knee. There is no normally organized elastin or reticulin in the soft tissues surrounding the knee, but these structures are capable of approximately lengthening by approximately 10% before failure (i.e., loss of elastic deformation and recovery). Generally, this is approximately 2 mm, which translates to approximately 10° of motion lost after closure.

Any varus or valgus malalignment must be compensated by removal of osteophytes and by appropriate medial or lateral ligament and soft tissue release, (i.e., concave balancing). Flexion and extension deformities are managed with a combination of bony resection, soft tissue release, and possibly posterior cruciate release.

The placement of the tibial plateau is also important. Aside from establishing proper rotation, posterior placement of the tibial plateau may be useful to:

1) compensate for shortening of the femur by allowing the tibia to move posteriorly under the femur;
2) decrease posterior impingement and roll-back;
3) decrease posteromedial tibial wear;
4) decrease posterior soft tissue impingement; and
5) allow for maintenance of the posterior cruciate ligament if the femur is shortened only a few millimeters; and
6) decrease patellofemoral pressure by anteriorly placement of the tibial tubercle relative to the femur.

If the femur 1 is shortened more than approximately 4 mm from "anatomic," a surgeon should consider releasing the posterior cruciate ligament to allow the tibial prosthesis to fall back under the femoral prosthesis in flexion. In addition, releasing the posterior cruciate ligament allows increased laxity in flexion. Generally, up to 4–5 mm of extra space can be achieved in flexion and 0–2 mm in extension.

The PCL then is released if:
1) the femur is shortened more than 4 mm;
2) flexion under anesthesia is less than 115°; or
3) fixed varus deformity.

Referring now to FIGS. 21–33, once the bore 21 is formed longitudinally in the shaft 9 and in the condylar region 4 of the femur 1, the tool 30D is fitted over the rod 20 until it contacts the distal femur, i.e., the distal end of the femur 1. Before the tool 30D is fitted over the rod 20, the tool 30D is first fitted with a collet 206 which is similar to the stub 24. Like stub 24, collets having different angles varying about 5–7° may be provided and selection is made based on the sex, anatomical condition and other conditions of the patient. The collet 206 is similar to the valgus angle bushing available from Smith & Nephew Richards, Inc.

The tool 30D is somewhat similar in structure to the valgus alignment guide and valgus alignment assembly available from Smith & Nephew Richards, Inc. The tool 30D includes a lower half 208 and an upper half 210 slidable in the lower half 208. The lower half 208 includes a pair of posterior caliper feelers 47 for respectively contacting the posterior surfaces of the medial and lateral condyles. The caliper feelers 47 can be elongated to accommodate smaller and larger femurs, corresponding to prosthesis sizes 1–5 and 4–8 respectively.

The tool 30D includes a graduated scale 212. The graduated scale 212 includes markings 213 on the upper half 210 and a marker 214 on the lower half. The markings 213 on the graduated scale 212 indicate prosthetic sizes and hence is a measure of the distance D or S. For example, the markings 213 in FIG. 21 indicate prosthetic sizes 3–8. The upper half 210 can be adapted to indicate other prosthetic sizes as well.

The lower half 208 includes scale 215 to indicate differences in size between respective prosthetic sizes, i.e., the number of millimeters over or under the prosthetic size. In a preferred embodiment, the scale 215 is calibrated in one millimeter increments. The calibration is such that when the marker 214 directly corresponds with a mark 213 on the scale 212 for a particular prosthesis, e.g., size 4, when this size 4 prosthesis is utilized, the difference between D and D' (the thickness $t_3$ resected at the posterior condyles and the distal femoral condyles) will be substantially equal to the thickness S FIG. 4 of the size 4 prosthesis to be inserted.

If the marker 214 falls between prosthesis markings 213 on scale 215, generally the smaller prosthesis size is selected and the resected thicknesses of the posterior condyles and the distal femur will be slightly increased accordingly. For example if the marker 214 falls one increment, i.e., one millimeter, beyond prosthesis size 4, then the resected thickness at the posterior condyles will be the average thickness of the posterior condyles of the size 4 prothesis (e.g., 19.5 mm) plus 1 mm. Similarly, the resected thickness of the distal femoral condyles will be the average thickness of the distal femoral condyles of the size 4 prosthesis (e.g., 9.5 m) plus 1 mm.

It should be realized that if a surgeon were to choose the larger prosthesis, then the marker 214 and the scale 215 would indicate how much less thickness from the prosthetic size would be resected at the posterior and distal femoral condyles. In this case, appropriate compensation must be made on the distal femoral resection and possibly the proximal tibial resection depending on the deformity of the knee to achieve satisfactory motion and ligament balance.

The tool 30D includes an anterior-posterior (A-P) measuring guide or anterior caliper feeler 64 which along with the posterior caliper feelers 47 measure distance D'. The A-P measuring guide 64 includes a tab 216 which allows the A-P measuring guide to be releasably attached to the tool 30D.

The A-P measuring guide 64 is somewhat similar in structure to a femoral sizing stylus available from Smith & Nephew Richards, Inc. The A-P measuring guide 64 includes a rod 63 and a sector plate 66 adapted to contact the anterior surface 13 of the femoral cortex. Unlike the tool 30 of the first preferred embodiment of FIGS. 1–3, the sector plate 66 need not be pivotally attached to the rod 63.

Figure 28:
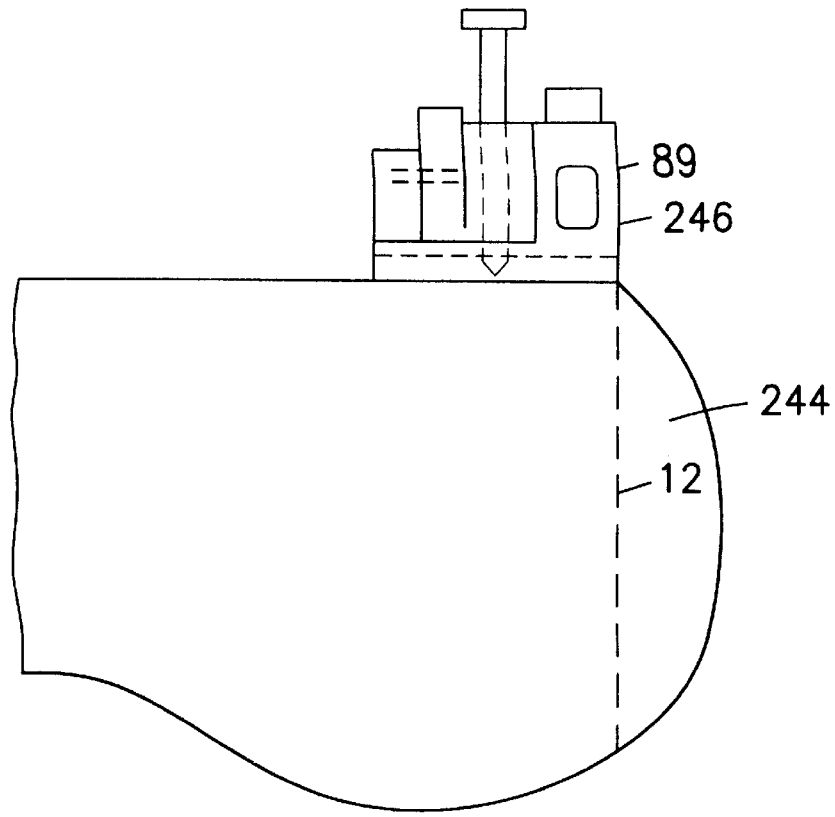
FIG. 28 is a side view of the femur with the distal cutting block mounted thereon.
Figure 32:
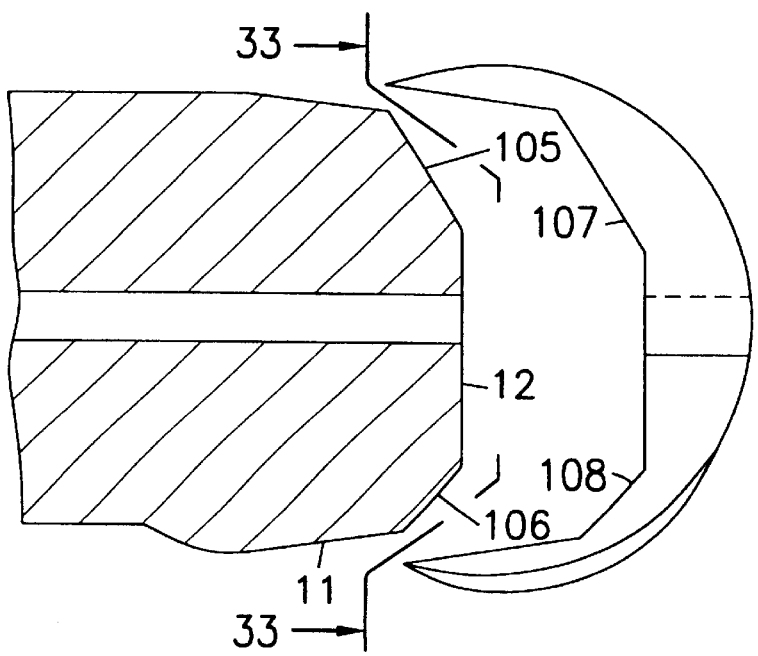
FIG. 32 is a side view of the distal end of a femur after it has been cut and a preferred prosthesis is ready to be mounted thereon.
Figure 29:
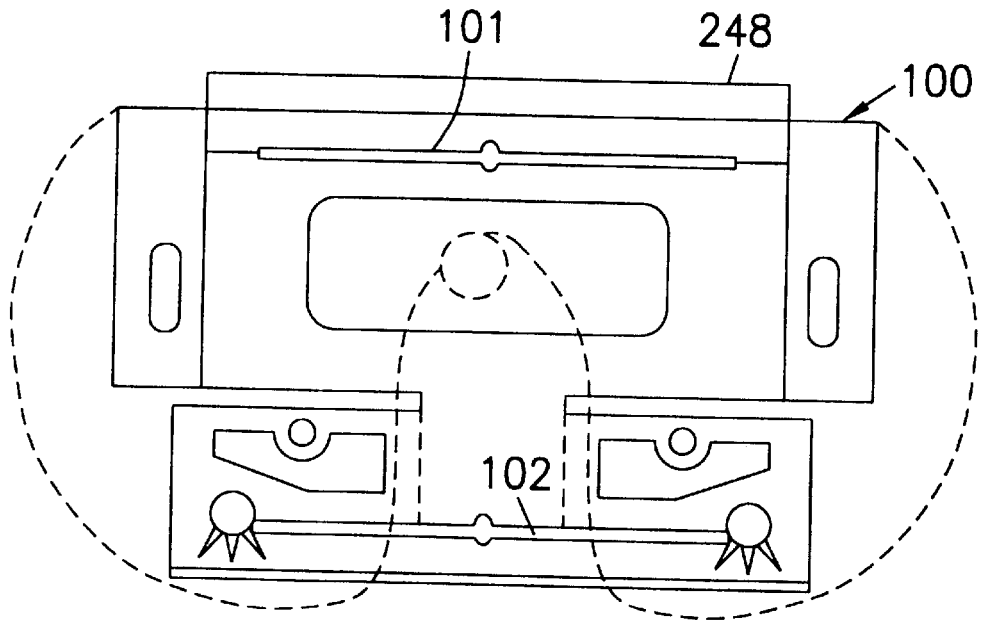
FIG. 29 is a top view of the A-P cutting block mounted on the distal femur.
Figure 30:
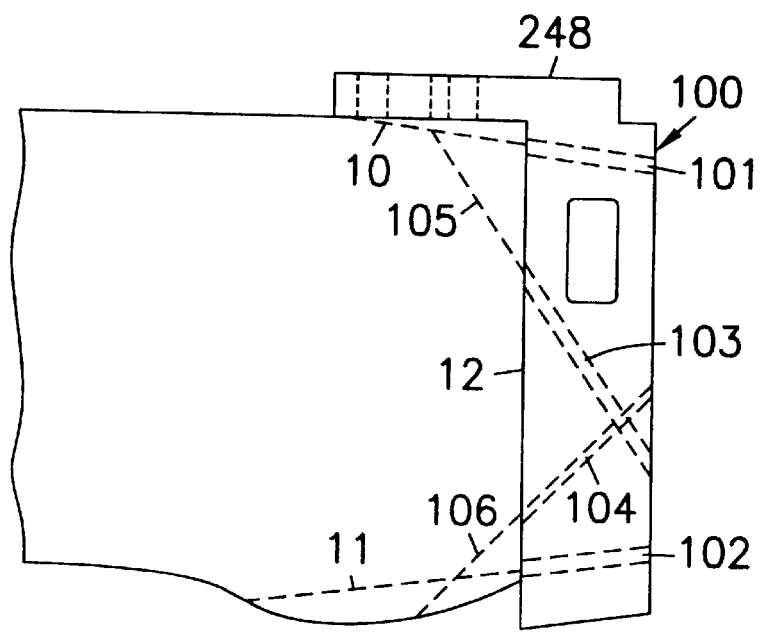
FIG. 30 is a view similar to FIG. 13 illustrating the distal end of the femur after the distal end has been cut and the A-P cutting block has been mounted thereon.
Figure 31:
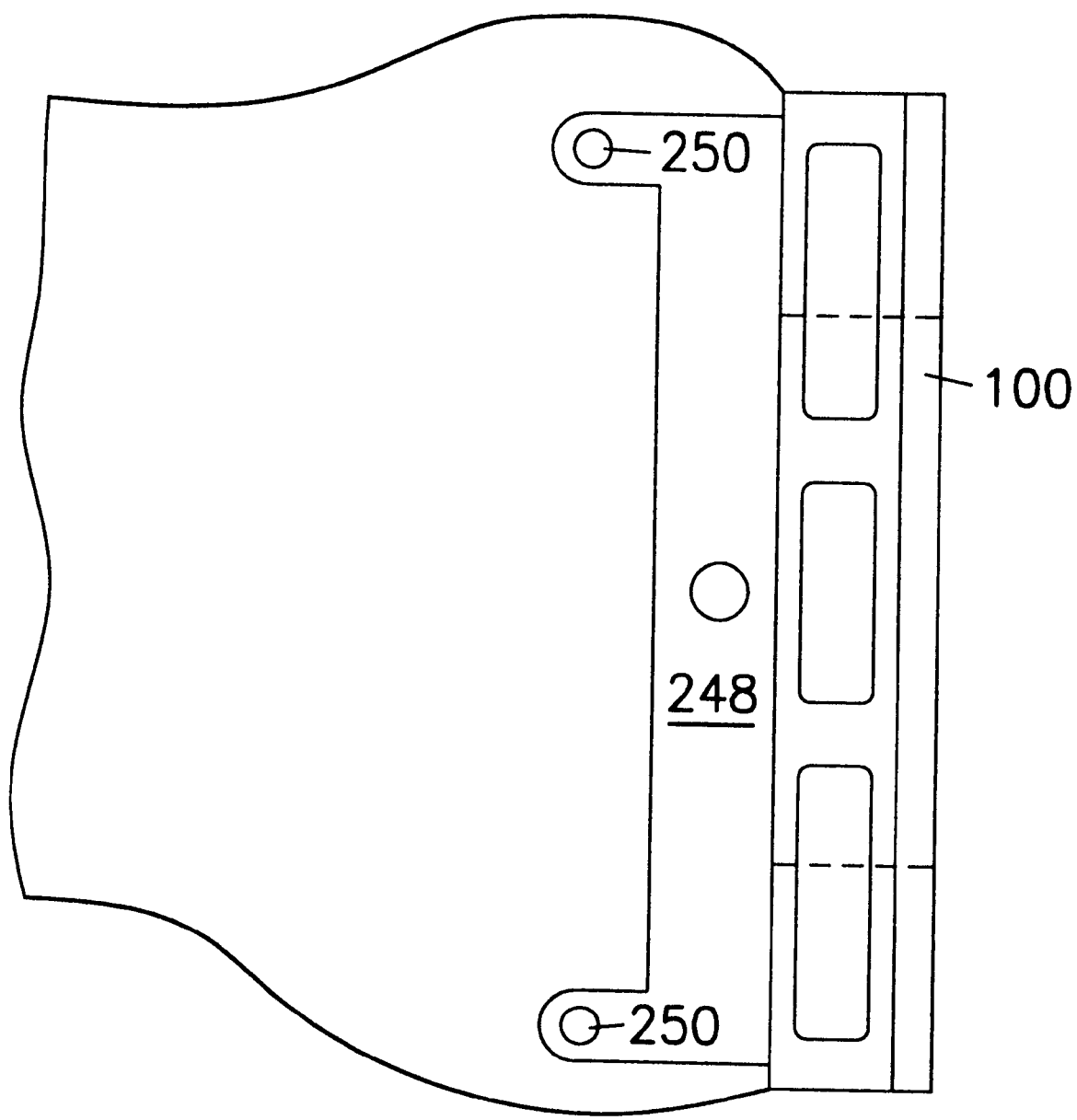
FIG. 31 is a top view of the A-P cutting block mounted on the distal end of the femur after the distal end has been cut and the A-P cutting block has been mounted thereon.

The tool 30D is also adapted to be used in connection with a distal cutting block 90 (FIGS. 24–28) and an A-P cutting block 100 (FIGS. 29–31). The distal cutting block 90 is used to resect the distal ends of the femur 1. The A-P cutting block 100 is used to resect the posterior medial and lateral condyles, to make the final anterior resection and to make the posterior and anterior chamfer resections as described above. The distal cutting block 90 and the A-P cutting block 100 are somewhat similar in structure to the distal femoral resection stylus and cutting block, and the femoral A-P cutting block, respectively, available from Smith & Nephew Richards, Inc. Like the A-P measuring guide 64, the distal cutting block 90 is releasably attached to tool 30D by tab 218.

Referring now to FIGS. 21–33, in use, once the tool 30D with the properly angled collect 206 is fitted over the rod 20, which is inserted in the bone 21 of the femur 1, the tool 30D is made to contact the distal femur 1. The side of tool 30D that contacts the distal femur 1 should include a 3 mm lateral offset 220 to contact the distal surface of the lateral femoral condyle. This ensures that the distal resection is substantially parallel to the proximal tibial resection in the medial lateral plane, and that the resultant distance between the tibial and femoral resections will be substantially equal to the thickness of the combined tibial and femur prosthesis in flexion and extension.

Next, external rotation must be oriented from the posterior condyles (or any other consistent anatomic landmark). This requires adjustable posterior feelers or "feet" 47 to contact the posterior condyles at 3° of external rotation, or to be able to compensate for deformities and achieve posterior rotation.

To achieve the 3° external rotation, the tool 30D is then rotated so that the posterior caliper feelers 47 contact both corresponding posterior surfaces of the medial and lateral condyles (FIGS. 22 and 23) assuming equal or no bone substance loss. This sets the rotation or angle of the preliminary anterior resection 10 and the posterior resection 11 which is made by the A-P cutting block 100 (FIGS. 29–31), and equal amounts of substance will be resected from the medial and lateral posterior condyles. The rotation or angle of the posterior resection 11 is also set because an anterior portion 248 of the A-P cutting block 100 rests on the preliminary anterior resection 10 and thus sets the posterior resection 11 at the same rotation or angle as the anterior resection 10. Nails 222 should then be inserted in nail holes 224 to secure the lower half 208 to the distal femur.

If the posterior surfaces have unequal bone loss, the corresponding caliper feeler 47 should be made to contact the posterior surface with the least amount of bone loss. The tool 30D should then be rotated on the rod 20 so that the other caliper feeler 47 corresponding to the posterior condyle with the greater amount of bone loss is a distance away from that posterior condyle about equal to the amount of bone loss. This sets the rotation, or angle, of the preliminary anterior resection 10 and the posterior resection 11 which is made by the A-P cutting block 100 (FIGS. 29–31). Unequal amounts of substance will now be resected from the medial and lateral posterior condyles.

In the first preferred embodiment of the invention, the scale 71 should be set to rotate the sleeve 31 and thereby the rod 20 through angle A at 1° for every millimeter of bone loss. For example if the surgeon determines that there is 2 mm bone loss at one of the posterior condyles, the index marker should be set to correspond to a 2° angle or the angle scale 73. The sleeve 31 is then rotatable locked in the slider 34 and the rod 20 is driven in the bone 21 of the femur 1 to be angularly secured thereon in the desired rotational position relative to the plane T targeted to the portion surface of the medial and lateral condyles. See FIG. 9.

In order to set the caliper means in position to measure the distance D', the nuts 50 on pins 44 are loosened and the upper and lower caliper halves 36 and 37 are rotated as a unit around pin 44 at the lateral femoral condyle until the index marker 72 returns to its zero setting on the scale 73 as shown in FIG. 10. The nuts 50 are then tightened and the caliper halves are now in a position to measure distances perpendicular to the plane P tangent to the posterior surface of the lateral condyle.

In the fourth preferred embodiment of the invention, the tool 30C is rotated to cause the end 24 to rotate through angle A corresponding to the 2° angle of rotation. The angle A is read in the angle scale 147.

It should be realized that as explained above, if a prosthesis other than a GENESIS II prosthesis is used, i.e., a symmetrical prosthesis, the posterior condyles will be resected asymmetrically to reflect the 3° external rotation that was otherwise built into the GENESIS II prosthesis. This angulation may be greater than or less than 3° to compensate for any bone loss posteriorly.

Figure 22:
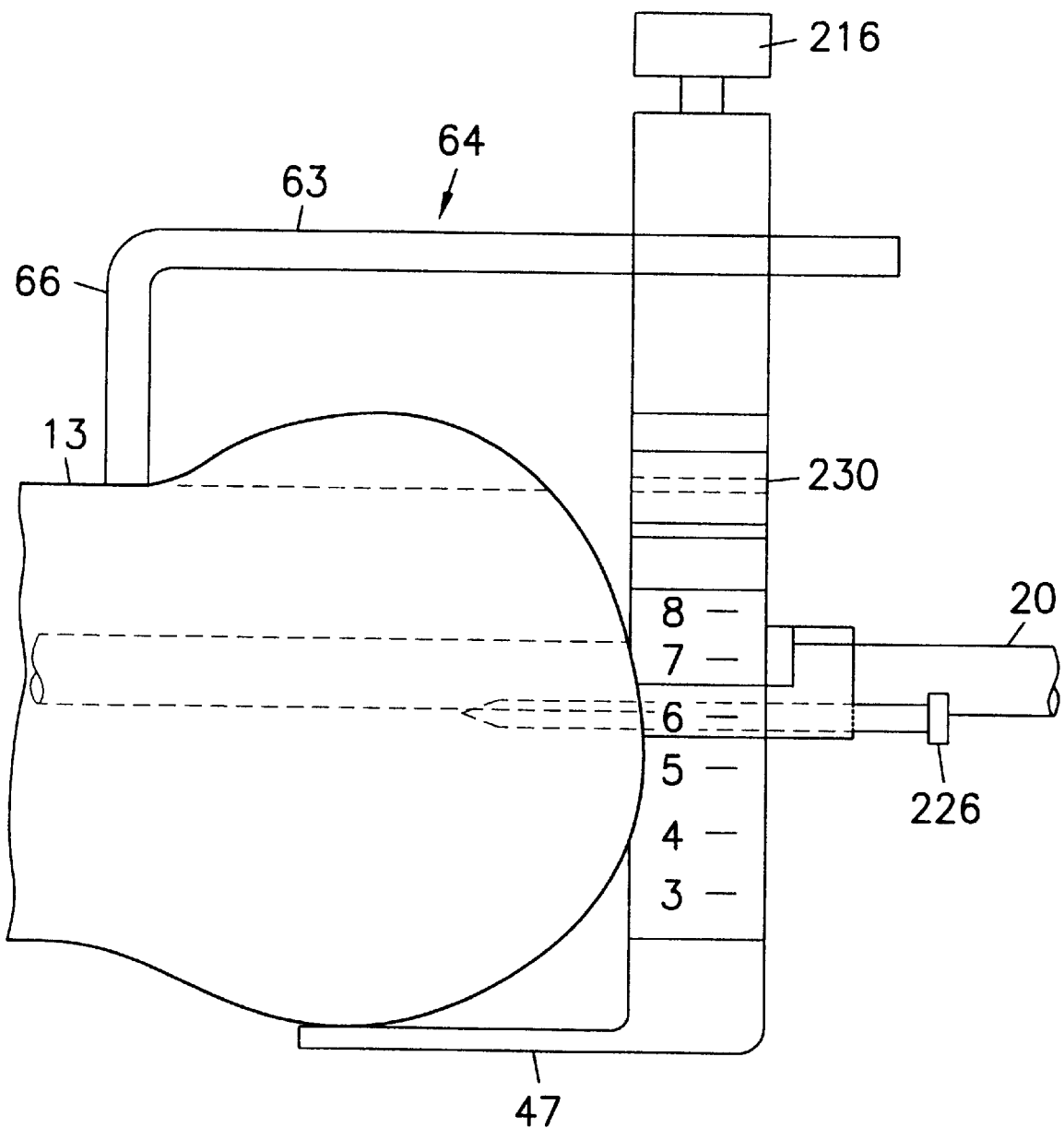
FIG. 22 is a side view similar to FIG. 5 of the tool of FIG. 21 mounted on the distal femur.
Figure 23:
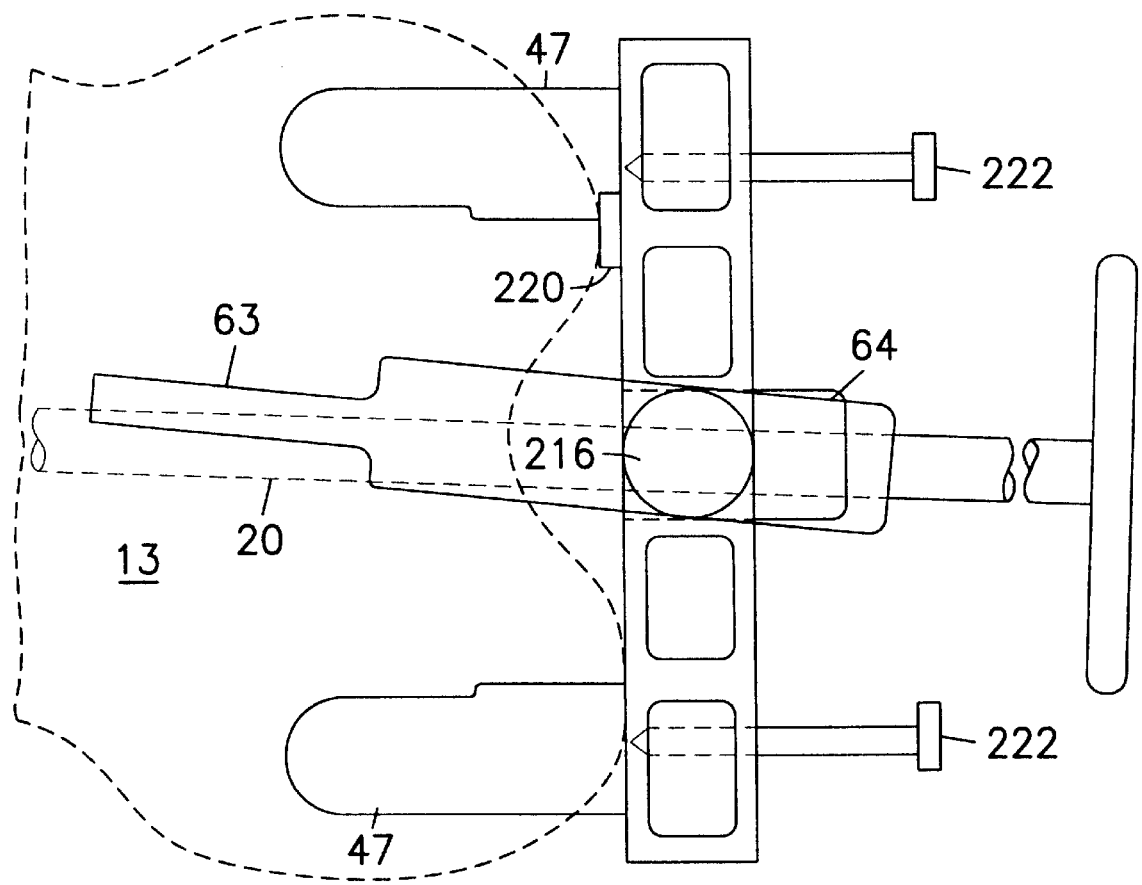
FIG. 23 is a top view of the tool of FIG. 21 mounted on the distal femur.
Figure 25:
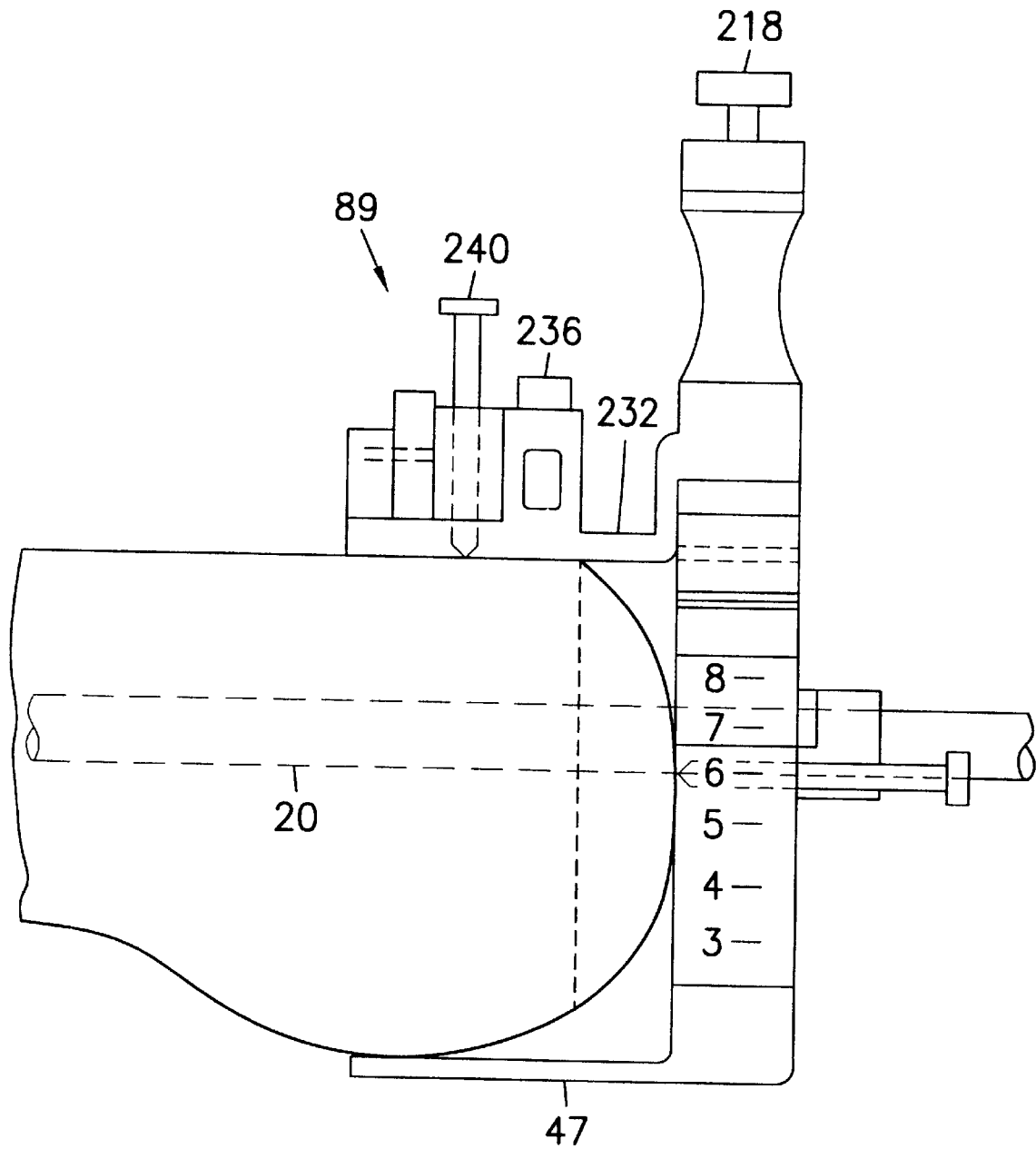
FIG. 25 is a side view of the tool of FIG. 21 mounted on the femur installed with the distal cutting block.
Figure 26:
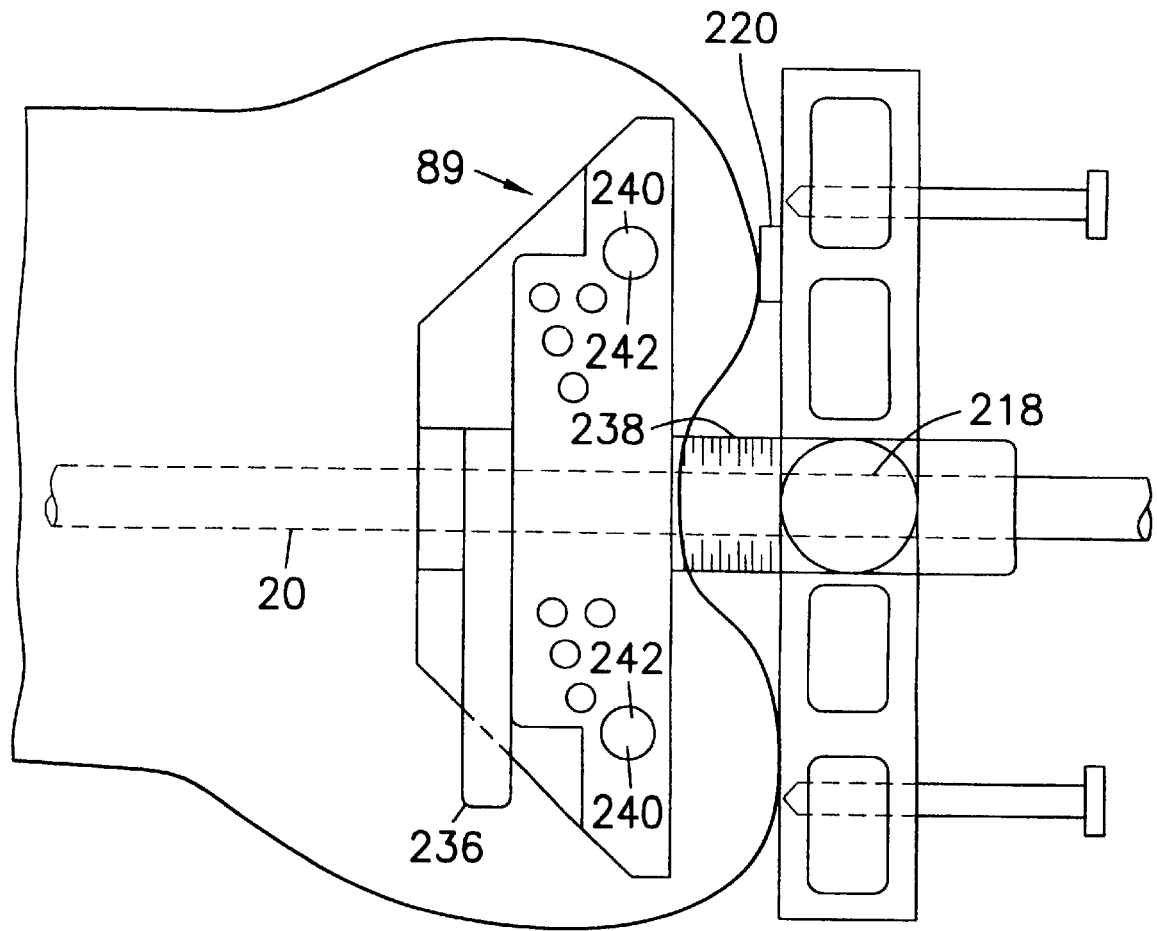
FIG. 26 is a top view of the tool of FIG. 25 mounted on the femur.

Referring back now to tool 30D, in order to set the caliper means in position to measure the distance D', the upper half 210 of the tool 30D fitted with the anterior caliper feeler 64 is then lowered until the sector plate 66 of the anterior caliper feeler 64 contacts the lateral portion of the anterior cortex, i.e., the sector plate 66 should contact the lateral side of the anterior cortex (FIGS. 22 and 23). The marker 214 then indicates a prostheses size S or distance D. If the marker 214 falls between two prosthetic sizes, normally the smaller prosthetic size is chosen. The upper half 210 is then fixed to the distal femur by inserting a nail 226 in the nail hole 228 that corresponds to the smaller chosen prosthetic size.

A measurement is now made to determine the appropriate size A-P cutting block 100 to later be used to resect the posterior medial and lateral condyles. The approximate size cutting block 100 corresponds to the chosen prosthetic size. If the marker 214 fell between two prosthetic sizes and the smaller size is chosen, a measurement must be made to determine how many millimeters extra would be resected posteriorly. This measurement is then taken from the scale 215 and is equal to the number of millimeters the marker 214 is away from the smaller prosthetic size. This measurement is then added to the average thickness of the posterior condyles of the prosthesis to determine the posterior resections. Each type of prosthesis has its own average thickness. For example, if the marker 214 indicates 1 mm greater than prosthetic 198 size 3, 1 mm extra will be resected posteriorly. The total posterior resection would then be the average thickness of the posterior condyles of the prosthesis 198 (e.g., 9.5 mm) plus 1 mm for a total thickness of 10.5 mm.

With the tool 30D still mounted on the rod 20, the anterior caliper feeler 64 is removed from the upper half 210 by depressing the tab 216. A saw blade, not shown, is then inserted into guides or slot 230 to make a preliminary cut of the anterior condyles to meet the surface of the anterior cortex in proper rotational alignment in the mediolateral plane.

The distal cutting block 90 is then attached to the upper half 30D. The distal cutting block 90 includes a distal femoral sizer 232 that is releasably attached to cutting block 90 through a channel 234 fixed therein. The femoral sizer 232 is secured to the cutting block 90 by a cam mechanism 236 and to the upper half 210 by the tab 218.

The distal femoral sizer 232 includes a sliding scale 238 that is calibrated at one millimeter increments from the average size or thickness of the distal femoral condyles of the prosthesis. The average size or thickness of the distal femoral condyles of a prosthesis ranges from about 6 mm to 12 mm depending on the particular prosthesis chosen. A typical thickness of the distal femoral condyles of prosthesis 198 is about 9.5 mm.

The distal cutting block 90 should be inserted on the upper half 210 until it abuts the resected surface of the anterior cortex (FIG. 29). The cutting block should then be set at "size" (prosthetic size), plus (or minus) the previously taken measurement of how many extra (or fewer) millimeters would be resected posteriorly, i.e., 1 mm. The cutting block 90 is then locked into place on sliding scale 238 by the cam mechanism 236. The cutting block 90 is then secured to the anterior cortex by nails 240 through nail holes 242.

The rod 20 is then removed from the tool 30D. The cam mechanism 236 is disengaged and the distal femoral sizer 232 and the tool 30D should be removed from the distal femoral cutting block 90. Only the distal femoral cutting block should remain on the femur 1 (FIG. 28).

The distal femur should then be resected along the mediolateral plane 244 of the distal end 246 of the cutting block 90. The preliminary anterior and final distal cuts 10 and 12, respectively, have now been made.

The plane 246 or cut 12 should be substantially parallel in the mediolateral plane to the proximal tibial resection, i.e., parallel to the floor, assuming normal ligament balance. If the ligaments are not normally balanced, then the ligaments should be released by any of the known methods until the planes are parallel in the mediolateral direction.

Referring now to FIGS. 29–32, the distal cutting block 90 should be removed from the distal femur, and the appropriately sized A-P cutting block 100 should be inserted thereon. The A-P cutting block 100 is used to make the final anterior resection 10 and to resect the posterior surfaces of the medial and lateral condyles 11.

The A-P cutting block 100 is placed onto the distal femur secured by angled nails through the sides of the cutting block 100, not shown. The A-P cutting block 100 includes an anterior portion 248 that sits flush with the anterior cortex of the femur 1. If desired, the A-P cutting block 100 can also be secured to the distal femur by nails (not shown) in nail holes 250). The A-P cutting block 100 should now sit flush with the cut anterior surface 10 and the distal surface 12.

The A-P cutting block 100 includes slots 102 and 101 which are precisely placed for guiding a resector or cutting blade to produce the final posterior and anterior cuts 11, 10 respectively. Because of the asymmetric buildup of metal on the posterior condyles of the GENESIS II femoral prosthesis 198, e.g., 2.5 mm thicker on the posterior lateral condyle, the posterior femoral resection 11 must be altered to accommodate this difference. The resultant posterior femoral condylar joint line should be parallel to the resultant tibial joint line, i.e., parallel to the floor.

The posterior femoral resection 11 should be approximately 3° of varus in the mediolateral plane referenced from the horizontal assuming no wear or equal wear posteriorly. The A-P cutting block 100 assures this due to its alignment with the preliminary anterior femoral condyle resection 10. The A-P cutting block 100 is so aligned because the anterior portion 248 rests on the preliminary anterior cut 10 which has already been resected at the desired rotation or angle. The posterior condylar resection will be equal posterior medially and posterior laterally assuming no wear or equal wear of the posterior condyles. Moreover, the posterior cut 11 will be made parallel to the preliminary anterior 10 cut in the mediolateral plane.

As explained above, if there is no or equal wear, then tool 30D would have been rotated appropriately to account for the asymmetric loss of substance. The posterior resections will not be equal posterior medially and laterally under this circumstance.

The A-P cutting block 100 also includes angular slots 103 and 104 to form chamfer cuts 105, 106 which also match corresponding angular surfaces 107, 108 on the prosthesis 198. Preferably, the femur 1 should be resected in the following order: the posterior resection 11, the posterior chamfer 106, the final anterior resection 10 and the anterior chamfer 105. The A-P cutting block 100 is then removed and the prothesis 198 is installed on the distal femur by any of the known methods.

If certain "special situations" arise when performing the aforementioned procedures, certain modifications may be made as described below:

Varus Deformity:

19 mm must be resected from the convex side. When using a femoral resection guide, under-resect the distal femur by 3 mm (or use 3 mm offset 220) if the guide contacted the lateral femoral condyle (i.e., loss of medial femoral condyle with varus deformity). If there is asymmetrical loss of substance from the posteromedial femur, then less posterior angulation (e.g., 0°) may be proper. Then, resecting 11 mm from the lateral tibial plateau and doing a medial ligament resection will give a 19 mm rectangular space. Releasing the PCL with a fixed varus deformity and then performing a medial release as necessary is the preferred method.

Valgus Deformity:

With a valgus knee, assuming no medial laxity, the distal femoral resection proceeds as normal. If there is asymmetrical loss of substance from the posterolateral femur, then greater posterior angulation (e.g., 6°) may be proper. The tibial resection, however, should be referenced from the medial tibial condyle (e.g., at 8 mm) to complement the medial femoral resection. Then perform a lateral ligament release as necessary.

Loss of Flexion With Full Extension:

The posterior resection must be increased to achieve better flexion. If the PCL is released, an additional 10° can be achieved (the other 10° or 2 mm is lost to normal laxity). By over-resecting one size (i.e., 4 mm), an extra 20° of flexion can be achieved. If between sizes, an extra 15° can be achieved by over-resecting 3 mm to near the next smaller size. As an alternative, an extra few degrees can be achieved by resecting less bone from the distal femur and correspondingly more from the proximal tibia. In this way, both femoral and tibial components may be downsized.

Posterior femoral resection greater than an extra 4–7 mm (i.e., at least one full size smaller) seems to cause very little increase in flexion due to either bony impingement or quadriceps tightness. More significant loss of flexion may require other releasing, such as quadricepsplasty for exposure and mobility.

Loss Of Extension With Full Flexion:

Twenty-five to 30° loss of extension can be managed by posterior osteophyte excision, posterior capsular release, and distal femoral bony resection, up to an extra 4 mm as needed.

Procedurally, the surgeon should perform a preliminary anterior resection, choose the proper A-P size from the sizing guide, resect distally as prescribed, apply the A-P sizing block and resect posteriorly. Then excise the posterior osteophytes and posterior capsular release, and put in the trial spacers. If acceptable, proceed to finish the distal femoral resection. If the knee will not hyperextend 10° at this juncture, resect up to an additional 4 mm from the distal femur (i.e., 1 mm bone=5° extension) and release the posterior cruciate ligament. Because of increased posterior laxity from releasing the PCL, over sizing the femur (i.e., choosing the next larger size) may be desirable.

It should be realized that to achieve better results with total knee replacement, orthopedic surgeons must:

1) have accurate measurements;
2) have coordinated measurements;
3) maintain an "anatomic" joint line;
4) have access to dimensions of components; and
5) have the ability to compensate for deformities with a minimum of soft tissue release and bony resection.

Although the invention has been described with reference to specific embodiments thereof, it will become apparent to those skilled in the art that numerous modifications and variations can be made within the scope and spirit of the invention as defined in the attached claims.

What is claimed is:

1. Apparatus enabling the formation of planar resections on a medial condyle and a lateral condyle of a femur to provide seating surfaces to receive a femoral prosthesis, said apparatus comprising:

a measuring system for indicating a distance between an anterior surface of the femoral cortex and a prospective planar resection from the posterior of the medial and lateral condyles taking into account any angular deviation between said prospective planar resection and a tangential plane tangent to the posterior surfaces of said medial and lateral condyles, said measuring system including a tangential contacting element adapted to be placed in a plane tangential to said medial and lateral condyles;

a measurement element pivotable relative to said tangential contacting element about an axis in said tangential plane, said measurement element being pivotable through an angle corresponding to said angular deviation between the prospective planar resection and said tangential plane;

an anterior contacting element to contact the anterior surface of the femoral cortex; and a scale between said anterior contacting element and said measurement element to indicate a distance therebetween, said scale including markings representing graduated sizes of prostheses and markings identifying and accounting for differences between said anterior contacting element to said measurement element distance, and a prosthetic size.

2. Apparatus as claimed in claim 1, wherein said measurement element and said anterior contacting element include respective legs slidably adjacent to one another.

3. Apparatus as claimed in claim 1, further comprising a longitudinal rod adapted to be inserted into a femur, said measuring system being loosely mountable on said rod for establishing an angular or rotational position in the femur as a datum from which the planar resections are made.

4. Apparatus as claimed in claim 3, further comprising a scale for indicating an angle between said rod and said measuring system.

5. Apparatus as claimed in claim 3, further comprising a cutting guide mountable on said measuring system while said measuring system is mounted on said rod, said cutting guide for guiding a planar resection from the distal ends of said condyles.

6. Apparatus as claimed in claim 5, further comprising means on said cutting guide for securing the cutting guide to the condyles while the condyles are being resected.

7. An apparatus as claimed in claim 5, wherein said measuring system further includes a sizer for positioning said cutting guide, said sizer including a graduated scale formed by markings corresponding to said prosthetic sizes and also indicating intermediate distances between prosthetic sizes, said markings also corresponding to said markings on said scale between said anterior caliper feeler and said measurement plate.

8. A method for forming planar resections on a medial condyle and a lateral condyle of a femur and on a proximal end of a tibia to form seating surfaces to receive a femoral prosthesis and a tibial prosthesis to properly articulate with each other and with a patellar prosthesis, said method comprising the steps of:

determining a prospective planar resection to be made from the posterior surfaces of said medial and lateral condyles of the femur at which a distance between an anterior surface of the femoral cortex and said prospective planar resection is substantially equal to an interior dimension of a femoral prosthesis to be fitted on the femur, said prospective planar resection producing resection of the medial and lateral condyles from the posterior surfaces of respective thicknesses which are not necessarily equal;

measuring respective thicknesses to be resected by said prospective planar resection of the medial and lateral condyles from the posterior surfaces;

resecting from the anterior surfaces of the medial and lateral condyles along a plane substantially flush with the anterior surface of the femoral cortex and along said prospective planar resection;

resecting a distal end of the medial and lateral condyles along a plane which produces respective resected thicknesses, not necessarily equal, at the medial and lateral condyles and wherein the thickness of the distal medial resection is substantially equal to the measured posterior medial condyle thickness to be resected and the thickness of the distal lateral resection is substantially equal to the measured posterior lateral condyle thickness to be resected; and measuring the thickness or level to be resected from the proximal end of the tibia so that an average joint line of the fitted femoral prosthesis is at or near an anatomic level for a patient being fitted with the femoral prosthesis.

9. A method as claimed in claim 8, further comprising the step of resecting the measured thickness from the proximal end of the tibia.

10. A method as claimed in claim 9, wherein a resected space between the proximal tibial surface and the femur in flexion and a resected space between the proximal tibial surface and the femur in full extension are both substantially rectangular.

11. A method as claimed in claim 10, wherein a medial width of the resected space in extension equals the combined thickness of the tibial prosthesis at a medial portion thereof and the femoral prosthesis at a distal medial condyle thereof.

12. A method as claimed in claim 11, wherein a lateral width of the resected space in extension equals the combined thickness of the tibial prosthesis at a lateral portion thereof and the femoral prosthesis at a distal lateral condyle thereof.

13. A method as claimed in claim 12, wherein a medial width of the resected space in flexion equals the combined thickness of the tibial prosthesis at the medial portion thereof and the femoral prosthesis at a posterior medial condyle thereof.

14. A method as claimed in claim 13, wherein a lateral width of the resected space in flexion equals the combined thickness of the tibial prosthesis at the lateral portion thereof and the femoral prosthesis at a posterior lateral condyle thereof.

15. A method as claimed in claim 14, wherein the resected space in flexion must be equal to or greater than the lateral width of the resected space in extension.

16. A method as claimed in claim 8, further comprising the steps of:

loosely engaging a longitudinal rod in the femur such that an end of the rod projects from the femur;

mounting a tool on the projecting end of the rod; and orienting said tool to establish an angular position of said prospective planar resection at a determined angle with respect to a tangential plane at the posterior surfaces of the medial and lateral condyles, wherein the determined angle is within about plus or minus 15 degrees.

17. A method as claimed in claim 16, wherein the determined angle is about plus or minus 3 degrees.

18. A method as claimed in claim 8, further comprising the step of determining an angle of a plane along which said prospective planar resection at the posterior surfaces of the medial and lateral condyles is to be resected relative to a tangential plane at the posterior surfaces of the medial and lateral condyles.

19. A method as claimed in claim 18, wherein the determined angle of said prospective planar resection is substantially horizontal.

20. A method as claimed in claim 18, wherein the determined angle of said prospective planar resection is substantially parallel to a plane of the measured thickness or level to be resected from the proximal end of the tibia.

21. A method as claimed in claim 18, wherein the angle of the plane of the prospective planar resection places the femoral prosthesis in a proper rotational and angular alignment on the distal femur to reconstruct a normal and stable patellofemoral joint anteriorly and properly articulates the femoral prosthesis posteriorly and distally with the tibial prosthesis.

22. A method as claimed in claim 8, wherein the thickness or level to be resected from the proximal end of the tibia is measured so that the resected tibial surface is substantially level or horizontal.

23. A method as claimed in claim 22, wherein the thickness or level to be resected from the proximal end of the tibia is measured so that the angle of the proximal tibial resection corresponds to the angle of the distal femoral resection in extension.

24. A method as claimed in claim 8, further comprising the step of determining an angle of the plane of said prospective planar resection relative to a tangential plane at the posterior surfaces of the medial and lateral condyles.

25. A method as claimed in claim 8, further comprising the step of resecting said proximal tibial resection at the measured thickness or level.

26. An apparatus for enabling planar resections to be made on a medial condyle and a lateral condyle of a femur to form seating surfaces to receive a femoral prosthesis to properly articulate with a tibial prosthesis and a patellar prosthesis, said apparatus comprising:

means for measuring the thicknesses to be resected by a prospective planar resection from the posterior surfaces of the medial and lateral condyles of a femur at which a distance between an anterior surface of the femoral cortex and the prospective planar resection is substantially equal to an interior dimension of a femoral prosthesis to be fitted on said femur, said prospective planar resection producing resection of the medial and lateral condyles at said posterior surface of respective thicknesses which are not necessarily equal;

means for resecting from the anterior surfaces of the medial and lateral condyles along a plane substantially flush with the anterior surface of the femoral cortex, and along said prospective planar resection; and means for resecting a distal end of the medial and lateral condyles along a plane which produces respective resected thicknesses, not necessarily equal, from said medial and lateral condyles and wherein the distal medial resection is substantially equal to the measured posterior medial condyle thickness to be resected and the distal lateral resection is substantially equal to the measured posterior lateral condyle thickness to be resected.

27. An apparatus for enabling planar resections to be made on a medial condyle and a lateral condyle of a femur of a knee joint to form seating surfaces to receive a femoral prosthesis, said apparatus comprising:

means for obtaining a measurement of the femur at the knee joint and for selecting a suitable prosthesis size to be received based on the measurement obtained;

means for measuring a difference between the selected prosthesis size and the obtained measurement of the femur so as to determine a thickness to be resected along a plane through the posterior of said medial and lateral condyles; and means for guiding a planar anterior resection.

28. An apparatus as claimed in claim 27, further comprising means for enabling a thickness to be resected from a distal end of said medial and lateral condyles along a plane in accordance with the selected prosthesis size and the thickness to be resected through the posterior of said medial and lateral condyles.

29. An apparatus as claimed in claim 27, further comprising means to determine an angular or rotational position relative to the horizontal of the plane through which the posterior of said medial and lateral condyles are to be resected.

* * * * *

UNITED STATES PATENT AND TRADEMARK OFFICE
CERTIFICATE OF CORRECTION

PATENT NO. : 6,059,788  Page 1 of 1
DATED : May 9, 2000
INVENTOR(S) : Lawrence Katz It is certified that error appears in the above-identified patent and that said Letters Patent is hereby corrected as shown below:

Column 23,
Line 9, after "horizontal" insert -- in the medial-lateral direction when the tibia is in an upright position --.

Column 24,
Line 39, add new claims 30-32 as follows:

30. The apparatus as claimed in claim 1, wherein the tangential contacting element is a caliper plate.

31. The apparatus as claimed in claim 1, wherein the anterior contacting element is an anterior caliper feeler.

32. The apparatus as claimed in claim 1, wherein the measuring element is a measurement plate.

Signed and Sealed this

Eleventh Day of March, 2003

JAMES E. ROGAN
*Director of the United States Patent and Trademark Office*